US012758291B2

(12) United States Patent
Santos et al.

(10) Patent No.: US 12,758,291 B2
(45) Date of Patent: Oct. 13, 2026

(54) SURGICAL SCREW DELIVERY SYSTEM AND METHOD

(71) Applicant: Pro-Dex, Inc., Irvine, CA (US)

(72) Inventors: Daniel Manuel Santos, Irvine, CA (US); Justin Taber, Irvine, CA (US)

(73) Assignee: Pro-Dex, Inc., Irvine, CA (US)

( * ) Notice: Subject to any disclaimer, the term of this patent is extended or adjusted under 35 U.S.C. 154(b) by 643 days.

(21) Appl. No.: 18/181,454

(22) Filed: Mar. 9, 2023

(65) Prior Publication Data

US 2023/0285061 A1 Sep. 14, 2023

Related U.S. Application Data

(60) Provisional application No. 63/269,149, filed on Mar. 10, 2022.

(51) Int. Cl.
*A61B 17/88* (2006.01)
*A61B 17/00* (2006.01)
(Continued)

(52) U.S. Cl.
CPC ..................... *A61B 17/8875* (2013.01); *A61B 2017/00199* (2013.01); *A61B 2017/00734* (2013.01);
(Continued)

(58) Field of Classification Search
CPC ........... A61B 2017/00199; A61B 2017/00734; A61B 2017/564; A61B 2560/0443; B25B 23/045; B25B 23/06; B25B 23/02; B25B 23/04; B25B 23/065; B25B 23/08; B25B 23/147; B25B 23/16; B25B 23/00;
(Continued)

(56) References Cited

U.S. PATENT DOCUMENTS

| | | | |
|---|---|---|---|
| 4,936,169 | A | 6/1990 | Parsons |
| 5,203,864 | A | 4/1993 | Phillips |

(Continued)

FOREIGN PATENT DOCUMENTS

| | | | |
|---|---|---|---|
| WO | WO 2019/222771 A1 | 11/2019 | |
| WO | WO 2023/173008 | 9/2023 | |

OTHER PUBLICATIONS

International Search Report and Written Opinion in corresponding International Patent Application No. PCT/US2023/064030, mailed May 30, 2023, in 19 pages.

*Primary Examiner* — Marcela I. Shirsat
(74) *Attorney, Agent, or Firm* — Knobbe, Martens, Olson & Bear, LLP

(57) ABSTRACT

Various power screwdrivers with screw delivery systems are disclosed. In some embodiments, an apparatus attachable to a power screwdriver comprises a housing, a cartridge barrel having a plurality of barrel chambers, each capable of holding a screw and drive-bit assembly, and a drive shaft assembly. The drive shaft is aligned with a barrel chamber. The drive shaft has a handle sleeved thereon. The handle is coupled to a barrel cam connected to the cartridge barrel. Moving the handle proximally to a retracted position and then distally to a neutral position rotates the cartridge barrel in a way that the drive shaft is aligned with a barrel chamber adjacent the previous barrel chamber. Moving the handle distally to a forward position advances a screw out of a port.

17 Claims, 17 Drawing Sheets

(51) Int. Cl.

| | |
|---|---|
| ***A61B 17/86*** | (2006.01) |
| ***B25B 21/00*** | (2006.01) |
| ***B25B 23/04*** | (2006.01) |
| ***B25B 23/06*** | (2006.01) |
| ***B25B 23/08*** | (2006.01) |
| ***B25B 23/147*** | (2006.01) |

(52) U.S. Cl.
CPC ........... *A61B 17/865* (2013.01); *A61B 17/888* (2013.01); *A61B 17/8886* (2013.01); *A61B 17/8888* (2013.01); *A61B 2560/0443* (2013.01); *B25B 21/002* (2013.01); *B25B 23/04* (2013.01); *B25B 23/045* (2013.01); *B25B 23/06* (2013.01); *B25B 23/065* (2013.01); *B25B 23/08* (2013.01); *B25B 23/147* (2013.01)

(58) Field of Classification Search
CPC . B25B 23/0028; B25B 23/0035; B25B 15/00; B25B 21/00; B25B 21/002
USPC ........... 606/104, 53, 280, 300, 79, 86 R, 96, 606/98–99, 86 A, 86 B, 916
See application file for complete search history.

(56) References Cited

U.S. PATENT DOCUMENTS

| | | | | |
|---|---|---|---|---|
| 10,433,882 | B2 | 10/2019 | O'Neil et al. | |
| 2013/0123794 | A1 | 5/2013 | Walker | |
| 2015/0059139 | A1 | 3/2015 | Dantas | |
| 2020/0009710 | A1 | 1/2020 | Bethoux et al. | |
| 2020/0100799 | A1* | 4/2020 | Delman ................. | A61B 90/50 |

* cited by examiner

SURGICAL SCREW DELIVERY SYSTEM AND METHOD

CROSS REFERENCE

This application claims the priority benefit of U.S. Provisional Patent Application No. 63/269,149, filed Mar. 10, 2022, titled "Surgical Screw Delivery System", the entirety of which is incorporated by reference herein.

BACKGROUND

Field

This application relates to a system for providing fasteners, such as screws, to a powered medical device, such as a surgical screwdriver. The system can comprise a screwdriver attachment that serially and/or reciprocally loads screws onto the distal end of the screwdriver shaft so that each screw may be inserted into a patient with a more efficient workflow.

Description of Certain Related Art

In current surgical procedures, the time required for a surgeon to sequentially insert screws into the patient is increased by the time for each screw to be loaded onto the driver bit of a surgical screwdriver by a technician/nurse on the back table. Besides the operation of loading each screw, time is also lost since the screwdriver must be passed from the surgeon to the technician/nurse to load or reload the screw and from the technician/nurse back to the surgeon after loading the screw.

SUMMARY OF CERTAIN ASPECTS

There is a need to improve surgical workflow efficiency due to the high cost of operative time along with patient risk that increases with extended time under general anesthesia. Improving surgical workflow efficiency can reduce the time of an operation or other procedure, which can provide significant benefits. Reducing the operation or procedure time reduces the time a patient can be exposed to infections. Additionally, reducing the time of an operation or procedure allows the doctor, medical staff, and space (e.g., operating room) to be available for other procedures and tasks. Surgeons may have a financial incentive to improve their workflow efficiency. The time savings benefits can be immediately apparent to a surgeon at low upfront cost and do not need expensive studies or trials to prove effectiveness. This reduces development cost and risk.

The screw delivery system described herein can address one or more of the aforementioned concerns, or other concerns. In some embodiments, an apparatus forming part of the screw delivery system or power screwdriver comprises a housing configured to be attached to the screwdriver body. A shaft assembly can be coupled with the housing. The shaft assembly can have a proximal end and a distal end. A screw cartridge can be coupled with the housing. The screw cartridge comprises a cartridge barrel. The cartridge barrel can have a plurality of barrel chambers therein each configured to hold a screw, wherein the distal end of the shaft assembly can be substantially coaxially aligned with one of the plurality of the barrel chambers.

In some embodiments, the housing of the apparatus has a cavity, which can be an open cavity (e.g., open to the ambient environment). The screw cartridge and the shaft assembly can be disposed in the cavity of the housing. In some embodiments, the cartridge barrel of the apparatus can be cylindrically shaped with a barrel centerline generally parallel to a longitudinal direction of the screw delivery system. The plurality of barrel chambers can be formed through the cartridge barrel and can be uniformly distributed angularly within the cartridge barrel wherein the distance from each barrel chamber to the barrel centerline can be equal.

In some embodiments, the cartridge barrel is rectangularly shaped with a barrel centerline generally parallel to the longitudinal axis, wherein the plurality of barrel chambers are formed through the cartridge barrel with centerline of each barrel chamber generally parallel to the cartridge barrel centerline, distances between adjacent barrel chambers being equal.

In some embodiments, the screw cartridge of the apparatus comprises a cylindrical shaped revolver cam substantially coaxial with the cartridge barrel. The revolver cam can have curved grooves thereon and/or a cartridge shaft that can be substantially coaxial with the cartridge barrel. Each end of the cartridge shaft can be removably coupled with a snap feature disposed about the housing.

In some embodiments, the shaft assembly of the apparatus comprises a distal shaft at the distal end and a proximal shaft at the proximal end. The distal shaft can have a handle, such as a loading handle, sleeved thereon. The handle can allow the distal shaft to rotate therein. A cam-pin can be coupled to the handle and engaged with curved grooves on the revolver cam, wherein moving the handle proximally to a retracted position and then distally to a neutral position can cause the cartridge barrel to rotate around the barrel centerline to a position so that the shaft assembly is substantially coaxially aligned with the next barrel chamber in the cartridge barrel. In some embodiments, a compression spring can be sleeved on the distal shaft adjacent and proximal to the handle biasing the handle toward the distal end on the distal shaft.

In some embodiments, a port can be disposed about the distal end of the housing. The port can be substantially coaxial with the drive shaft assembly allowing a screw to be delivered through the port.

In some embodiments, the distal shaft and the proximal shaft can be extendably coupled by a shaft coupler so that the shaft assembly is extendable lengthwise but rigid rotation wise, wherein moving the handle distally to a forward position pushes the distal end of the distal shaft at least partially into the port.

In some embodiments, each screw can be configured to be held in a barrel chamber is pre-assembled with a drive bit. A shaft-to-drive-bit coupler can be disposed in the port. Both the inner surface of the port and the outer surface of the shaft-to-drive-bit coupler can be correspondingly (e.g., cylindrically) shaped, allowing the shaft-to-drive-bit coupler to rotate within the port. The shaft-to-drive-bit coupler can have a prism shaped internal channel that matches an external prism shape of the distal end of the distal shaft and an external prism shape of the drive-bit. In some embodiments, the prism shape is a hexagon shape.

In some embodiments, the proximal shaft can be coupled with at least one bearing, wherein the at least one bearing is coupled to the housing allowing the proximal shaft freely rotating therein. The proximal end of the proximal shaft can be flat shaped.

In some embodiments, the apparatus can be separably attached to a power screwdriver, power drill, or other surgical or medical handpiece, wherein the power screwdriver further comprises a handgrip, a screwdriver body, and a control panel comprising a user input and a light signal.

In certain aspects, the present technology comprises a method for delivering a plurality of screws, such as sequentially or serially. The method can comprise moving a handle that is connected to a cartridge and shaft module to a forward position, thereby moving one of a plurality of screws into a forward position, and wherein the cartridge and shaft module is detachably integrated with a power screwdriver disclosed above. The method can further comprise inserting the screw into a substrate, moving the handle proximally to a retracted position, moving the handle distally to a neutral position, repeating the steps of moving the handle to the forward position, inserting the respective screw, moving the handle proximally to the retracted position, and moving the handle distally to the neutral position. The method can further comprise determining that screw cartridge is exhausted (e.g., by determining that no screw comes out of the distal end of the port), and replacing the screw cartridge with another of the screw cartridge.

In certain aspects, a disclosed surgical screw delivery system comprises a housing having a longitudinal axis and a chamber, a handle assembly having a handle and a shaft wherein the handle assembly is configured to slide in a direction generally parallel to the longitudinal axis between a first position and a second position, a cartridge having a plurality of barrel chambers each of which is configured comprising a screw and a bit wherein the cartridge is configured to be removably received in the chamber. The surgical screw delivery system is configured such that each time the handle is moved from the first position to the second position the cartridge is rotationally indexed from one of the barrel chambers to another of the barrel chambers being aligned with the shaft.

BRIEF DESCRIPTION OF THE DRAWINGS

Certain features of this disclosure are described below with reference to the drawings. The illustrated embodiments are intended to illustrate, but not to limit the embodiments. Various features of the different disclosed embodiments can be combined to form further embodiments, which are part of this disclosure.

FIG. 21 is a partial cross-sectional view of the screw delivery system of

FIG. 20 showing some internal structures of the screw cartridge and the drive shaft.

DETAILED DESCRIPTION CERTAIN EMBODIMENTS

Various features and advantages of the disclosed fastener delivery technology will become more apparent from the following description of the several specific embodiments illustrated in the figures. These embodiments are intended to illustrate the principles of the disclosure. However, this disclosure should not be limited to only the illustrated embodiments. The features of the illustrated embodiments can be modified, combined, removed, and/or substituted as will be apparent to those of ordinary skill in the art upon consideration of the principles disclosed herein. No features, structure, or step disclosed herein is essential or indispensable.

1. Overview of the First Embodiment

Figure 1:
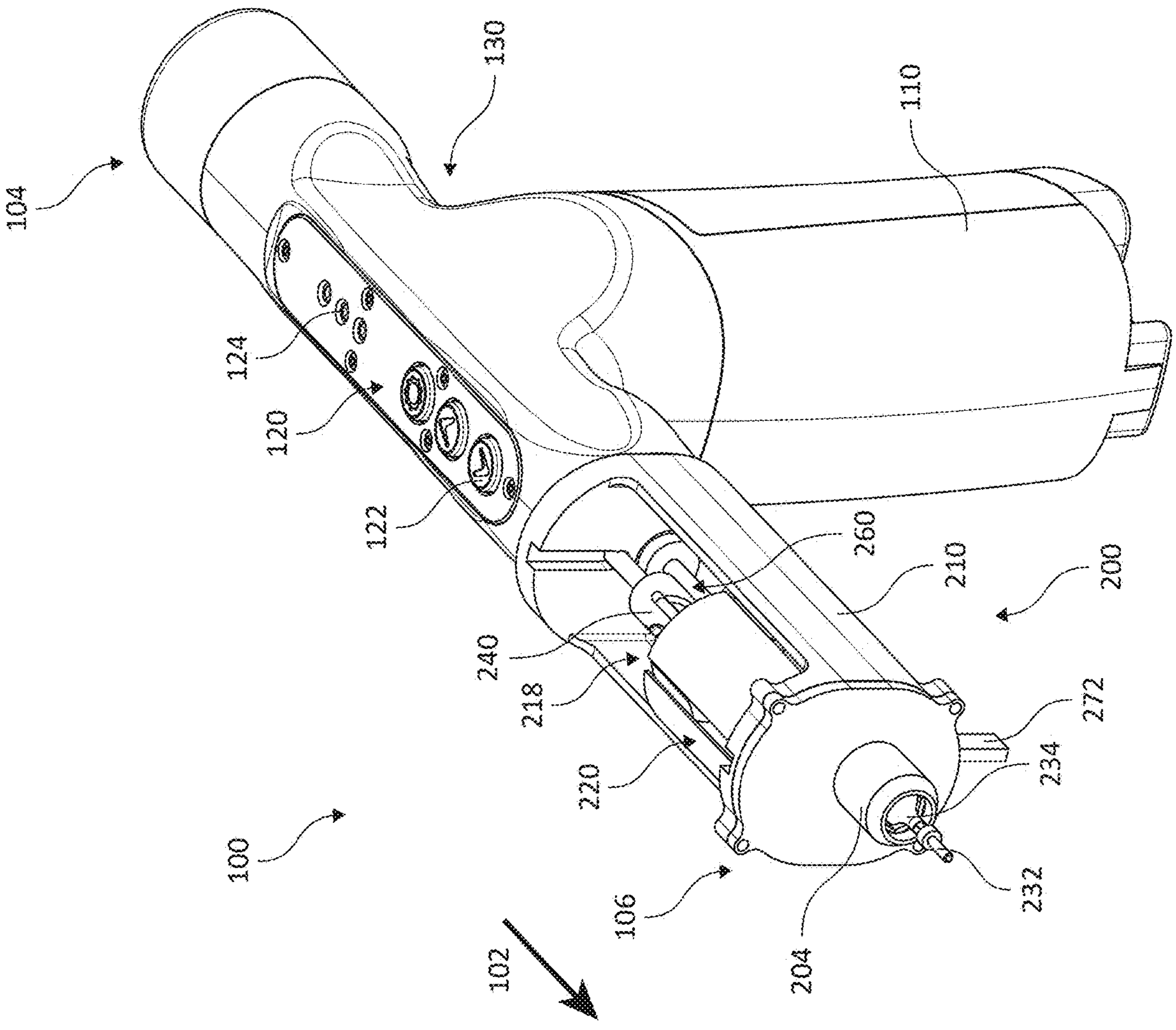
FIG. 1 is a perspective view illustrating an embodiment of a screw delivery system, with a screw loaded from a screw cartridge onto a drive shaft ready for operation.

Referring to FIG. 1, a perspective view of an example embodiment of a screw delivery system or power screwdriver 100 is illustrated. The screw delivery system 100 comprises a handgrip 110, a control panel 120, a screwdriver body 130, and a cartridge and shaft module 200. In FIG. 1, a longitudinal direction or axis 102 points from a proximal end 104 of the screw delivery system 100, which is toward the user (e.g., surgeon) during a surgical or medical operation, to a distal end 106 which is the distal end of the screw and shaft module 200. The cartridge and shaft module 200 can be detachably attached to the screw delivery system 100. The cartridge and shaft module 200 comprises a screw cartridge 220 that is configured to be loaded with a plurality of screw and drive-bit assemblies 230, and a drive shaft assembly 260. Each of the drive-bit assemblies can include a screw 232 and a drive-bit 234. The control panel 120 can be located at the top of the screwdriver body 130. The control panel 120 can comprise a plurality of control buttons 122 and a plurality of LED light signals 124 indicating the status of the screw delivery system 100.

As shown in FIG. 1, the screw and drive-bit assembly 230 (including a screw 232 and a drive-bit 234) extends out of a screw delivery port 204, ready to be inserted into a patient. It can be seen that at this state a handle 272 is located close to a first end, such as the distal end 104, or the distal end of the cartridge and shaft module 200. The handle 272 can have a cap or knob thereon for easy grasping.

Figure 2:
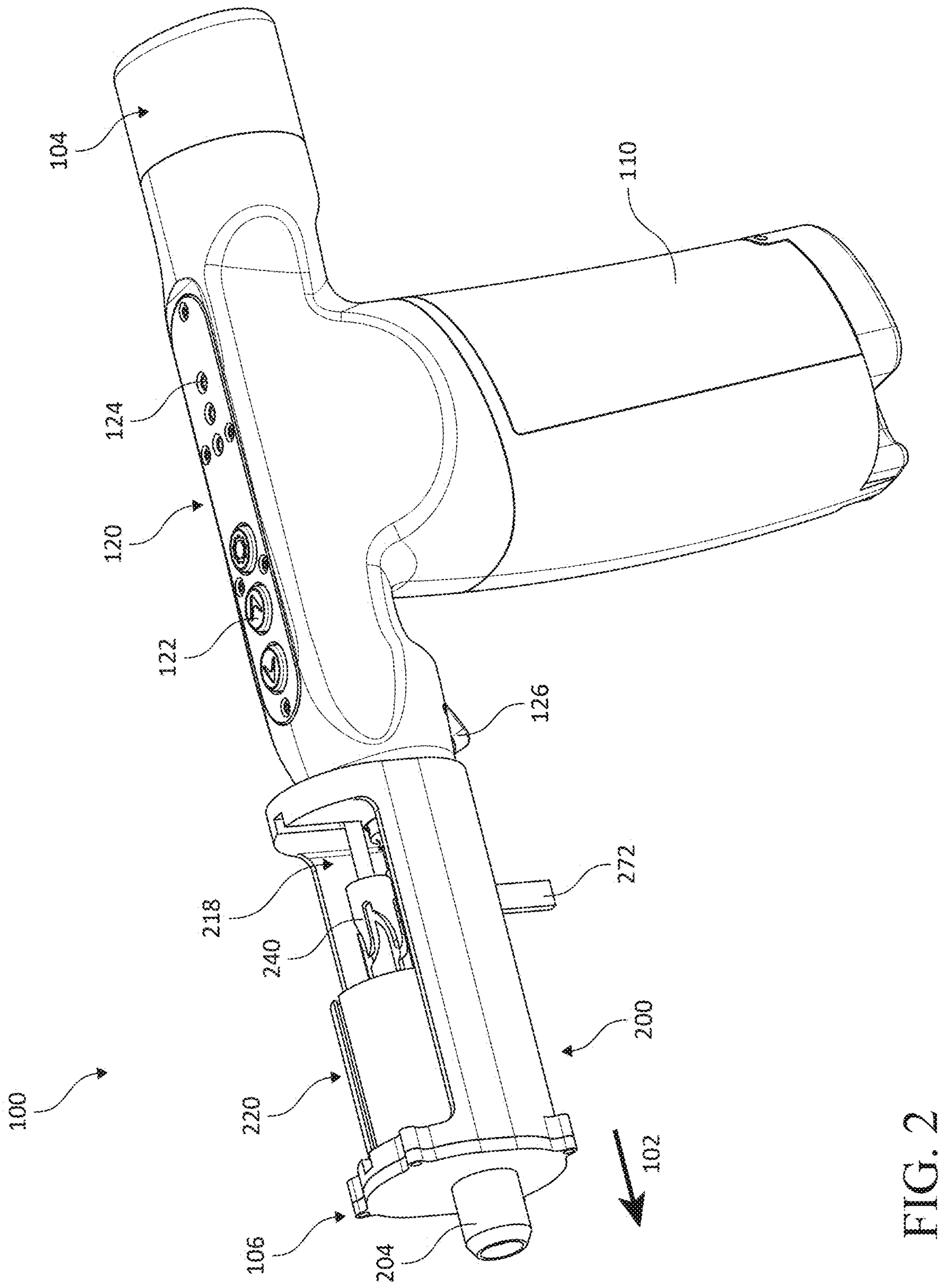
FIG. 2 is a perspective view of the screw delivery system of FIG. 1 with no screw loaded onto the drive shaft.

FIG. 2 depicts another perspective view of the screw delivery system 100 of FIG. 1, from a different viewing angle and in a different operational state. A difference is that no screw and drive-bit assembly 230 is extended out of the delivery port 204, and the handle 272 is located toward the proximal end of the cartridge and shaft module 200. In some embodiments, the housing 210 can have a through slot (see FIG. 5) on the bottom side to allow the handle 272 to move from the distal position shown in FIG. 1 and the proximal position shown in FIG. 2. As shown, an operation switch 126 can be disposed at the distal lower side of the screwdriver body 130 to work with the control panel 120 to operate the screw delivery system 100. For example, in some embodiments the operation switch 126 may have lateral and/or proximal-distal toggle positions to facilitate different operational functions, including forward and backward shaft rotations and start/stop of the screw delivery system 100.

Figure 3:
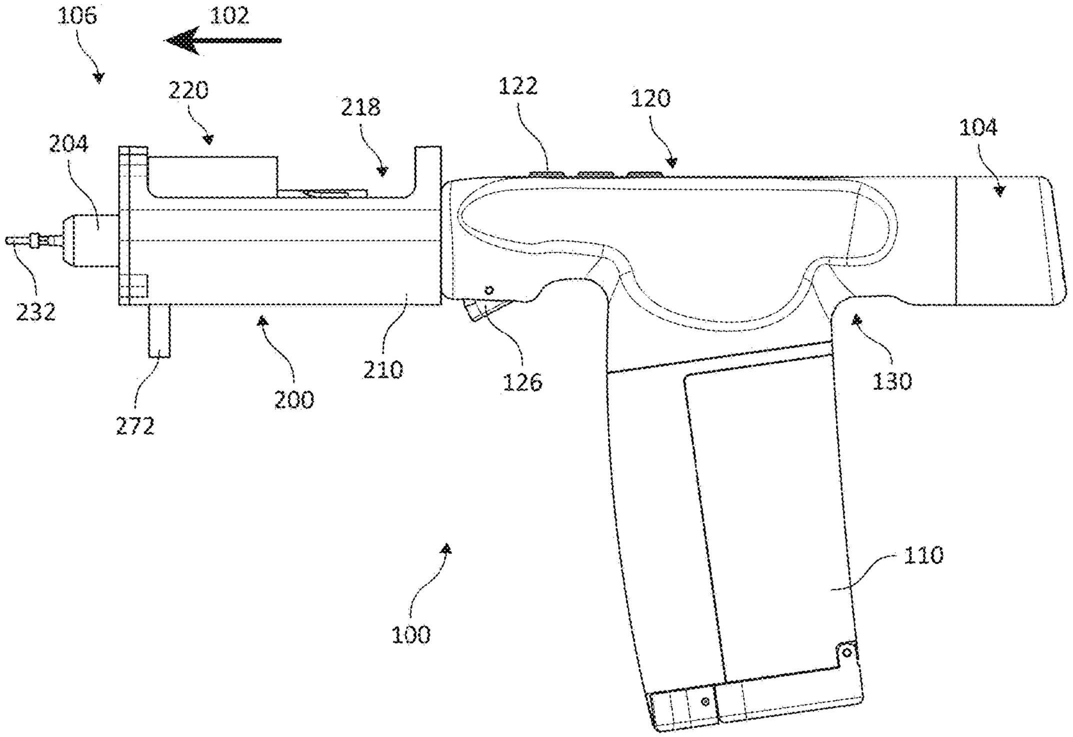
FIG. 3 is a front view of the screw delivery system of FIG. 1.
Figure 4:
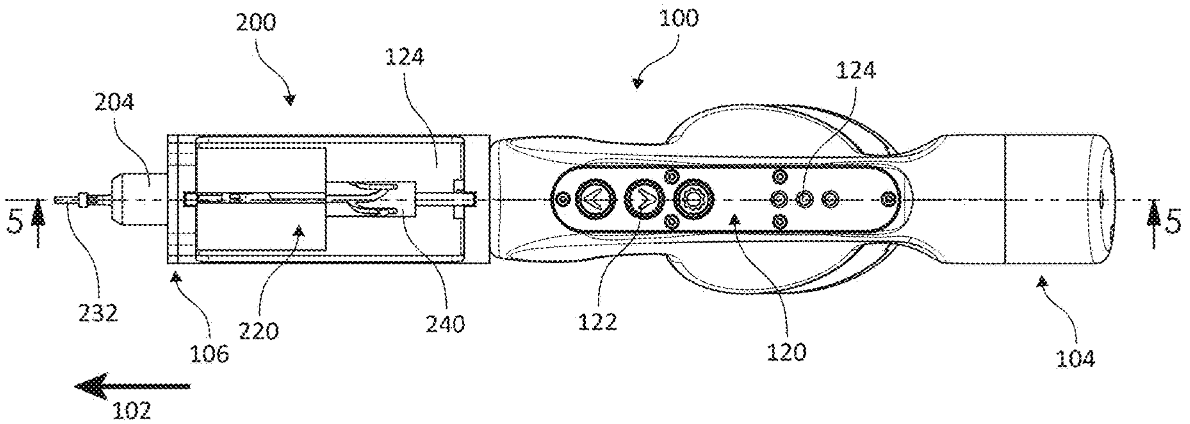
FIG. 4 is a top view of the screw delivery system of FIG. 1.

FIG. 3 and FIG. 4 are front and top views of the screw delivery system 100 respectively, at the operational state showing in FIG. 1 with a screw and drive-bit assembly 230 extending out of the delivery port 204. As illustrated, at least the screw (e.g., the distal tip) is exposed, which can facilitate accurate placement of the screw or other benefits. As shown, in some implementations, the entire length of the screw is exposed. The figures further illustrate certain components and features of the screw delivery system 100 in different viewing directions.

Figure 5:
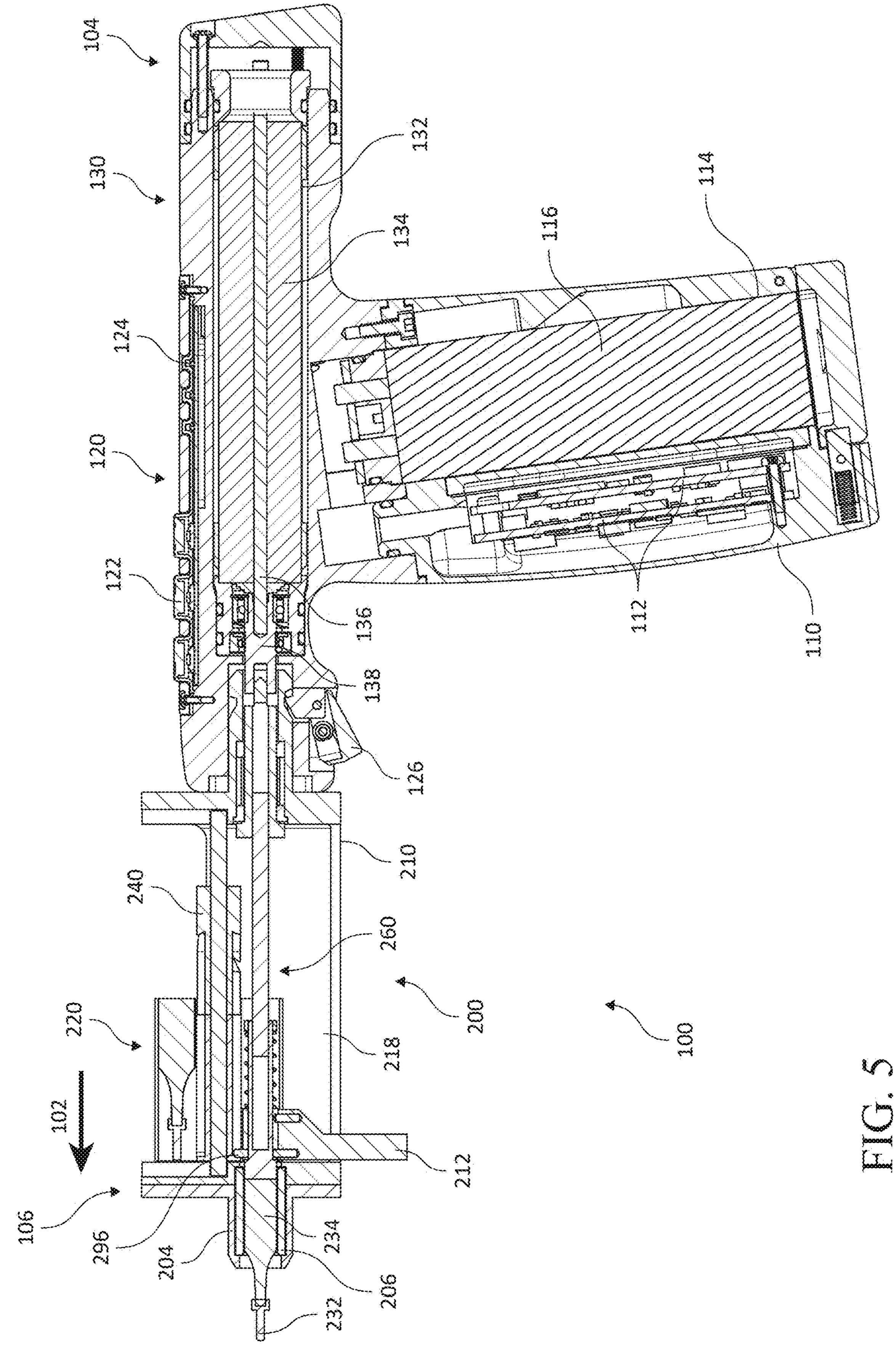
FIG. 5 is a cross-sectional view of the screw delivery system of FIG. 1 showing certain internal structures.

FIG. 5 is a cross-sectional view of the screw delivery system 100 of FIG. 1, revealing various internal structures. Inside the handgrip 110 can be housed one or more printed circuit boards (PCBs) for the operation of the screw delivery system 100 and a battery pack 116 held in a battery compartment 114. The battery compartment 114 may have a door that can be opened to access the battery pack 116. The battery pack 116 can comprise rechargeable batteries that can be charged either inside or out of the handgrip 110, or non-rechargeable batteries that are replaceable. The handgrip 110 may include a port to connect to an external power supply.

Inside the screwdriver body 130 can be a chamber 132 holding a motor 134, which can be powered by the batter pack 116 and operated by the operation switch 126 and control buttons 122 on the control panel 120 working with the PCBs 112. There may have gripping features in the motor chamber 132 for tightly holding the motor 134 so that during operation the motor 134 does not move rotationally or longitudinally relative to the screwdriver body 130. A motor shaft 136 extends out from the motor 134 at the distal end and couples to the drive shaft assembly 260 with a shaft coupler 138.

As shown in FIG. 5, the cartridge and shaft module 200 can be coupled with the distal end of the screwdriver body 130. In various embodiments, the cartridge and shaft module 200 is removably coupled with the screwdriver body 130. For example, the cartridge can be readily removed (e.g., when the screws in the cartridge have been deployed) and replaced with anther of the cartridge. In some embodiments, the coupling may be separable and may be keyed so that the cartridge and shaft module 200 is connected with the screwdriver body 130 in a fixed rotational orientation. Details of the cartridge and shaft module 200 and the operation of the screw delivery module 200 will be further discloses in the subsequent sections.

2. Cartridge and Shaft Module

Figure 6:
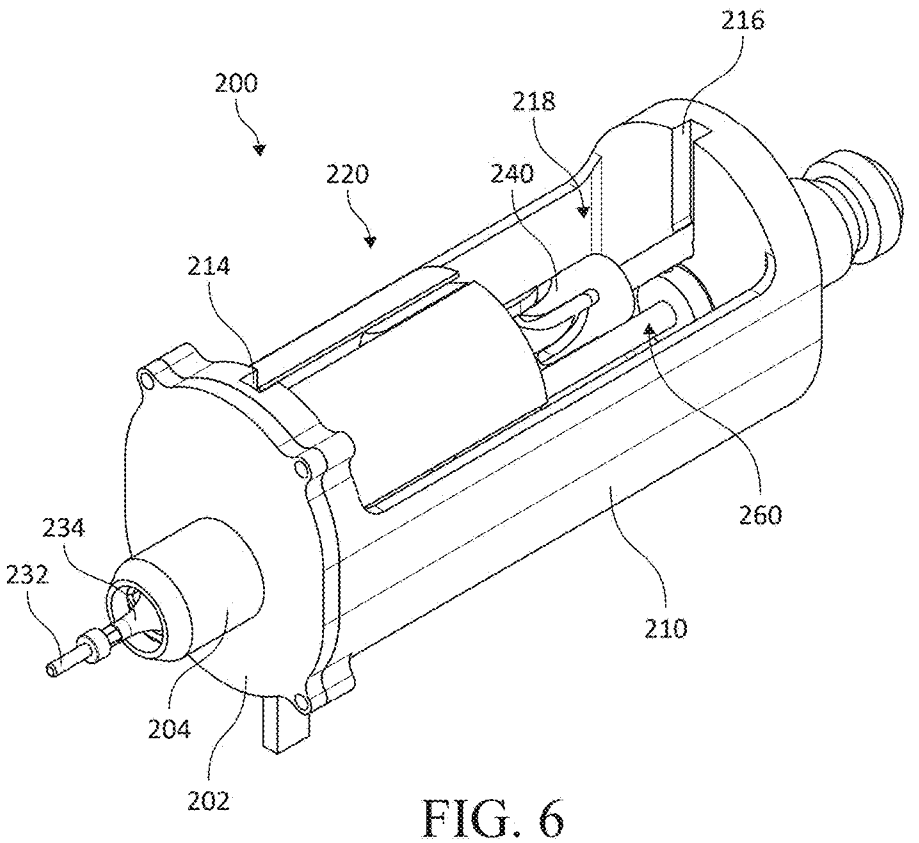
FIG. 6 is a perspective view of a cartridge and shaft module that detachably forms part of the screw delivery system of FIG. 1 with a screw loaded and sticking out a port, the cartridge and shaft module having a housing holding a screw cartridge and a drive shaft assembly.

Referring to FIG. 6, a perspective view of the cartridge and shaft module 200 is shown, at an operation state illustrated in FIG. 1 and FIGS. 3-5, where a screw 232 extends out of the delivery port 204 with a drive-bit 234 integrated. The cartridge and shaft module 200 comprises a housing 210 having a cavity 218 holding the screw cartridge 220 and the drive shaft assembly 260. As shown, the cavity 218 can be open, such as on a top. A first channel 214 and a second channel 216 can be formed on the walls of the cavity 218 at the distal end and proximal end respectively, configured to accept a cartridge shaft 236 which forms a part of the screw cartridge 220.

Figure 7:
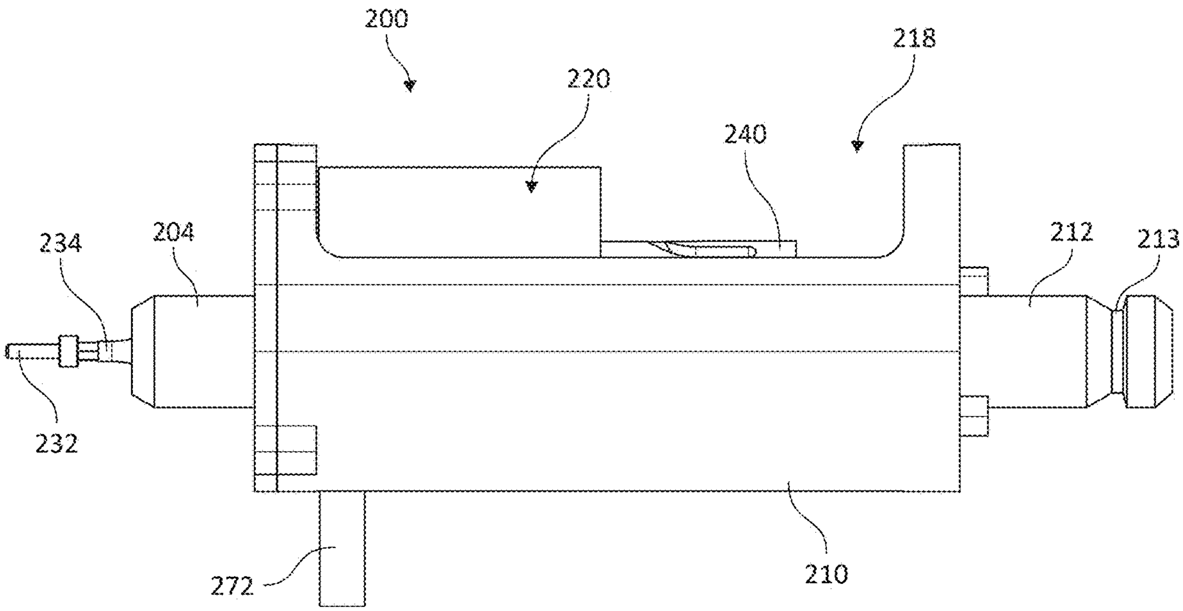
FIG. 7 is a front view of the cartridge and shaft module of FIG. 6.
Figure 8:
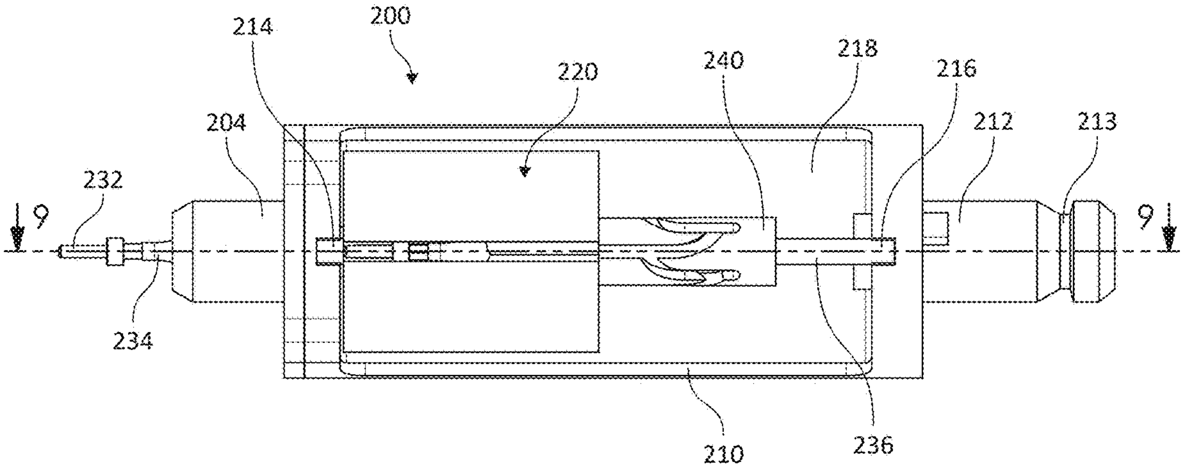
FIG. 8 is top view of the cartridge and shaft module of FIG. 6.
Figure 9:
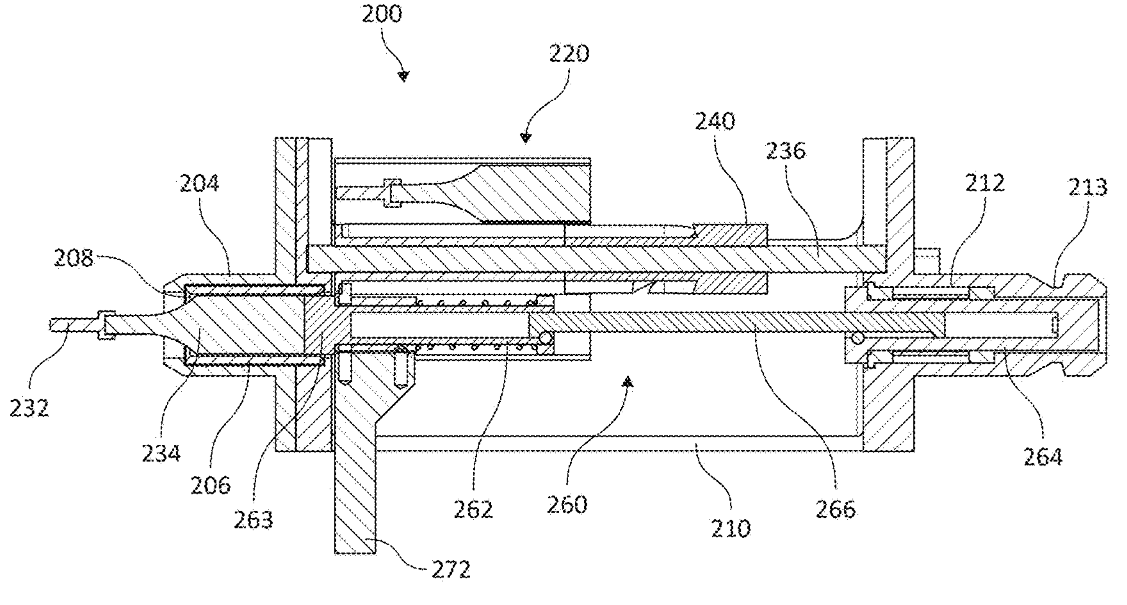
FIG. 9 is a cross-sectional view of the cartridge and shaft module of FIG. 6, showing certain internal structures.

FIG. 7 and FIG. 8 are front and top views of the cartridge and shaft module 200, respectively, in the state illustrated of FIG. 6, showing certain details in different viewing directions. FIG. 9 is a cross-sectional view of the cartridge and shaft module 200 of FIG. 6, revealing certain internal structures. As can be seen, the distal end and the proximal end of the cartridge shaft 236 are disposed in the first channel 214 and second channel 216 respectively. Each of the first channel 214 and the second channel 216 may include a securing mechanism (e.g., a resilient snapping feature, detent, etc.) to accept and hold an end of the cartridge shaft 236. In some embodiments, the securing mechanism may be formed as part of the channel, such as if the cavity 218 of the housing 210 is made of a plastic material. In some embodiments, the securing mechanism may comprise a spring, e.g., a leaf spring made of sheet metal or plastic. When snapped in the first channel 214 and second channel 216, the cartridge shaft 236 can rotate freely with minimal friction.

FIG. 9 also shows that the drive shaft assembly 260 is extended by a shaft adaptor 266 that can be extendably coupled with a distal shaft 262 at the distal end thereof and to a proximal shaft 264 at the proximal end thereof. When extended, the head portion 263 of the distal shaft 262 can be adjacent and/or in touch with (e.g., abutting) the drive-bit 234, and the interface of engagement is located within an internal channel 208 of a shaft-to-drive-bit adaptor 206. As will be described subsequently, the internal channel 208 has an inner shape matching to the shape of the drive-bit 234 and the shape of the distal shaft head 263, so that rotational movement and torque can be transferred from the shaft assembly 260 to the drive-bit 234 through the shaft-to-drive-bit adaptor 206.

FIGS. 6-9 also show a neck portion 213 formed on a protruded portion 212 at the proximal end of the housing 210. The neck portion 213 may help facilitate the coupling between the cartridge and shaft module 200 and the screwdriver body 130.

Details of the screw cartridge 220 and the drive shaft assembly 260 will be further described in the subsequent sections.

Figure 10:
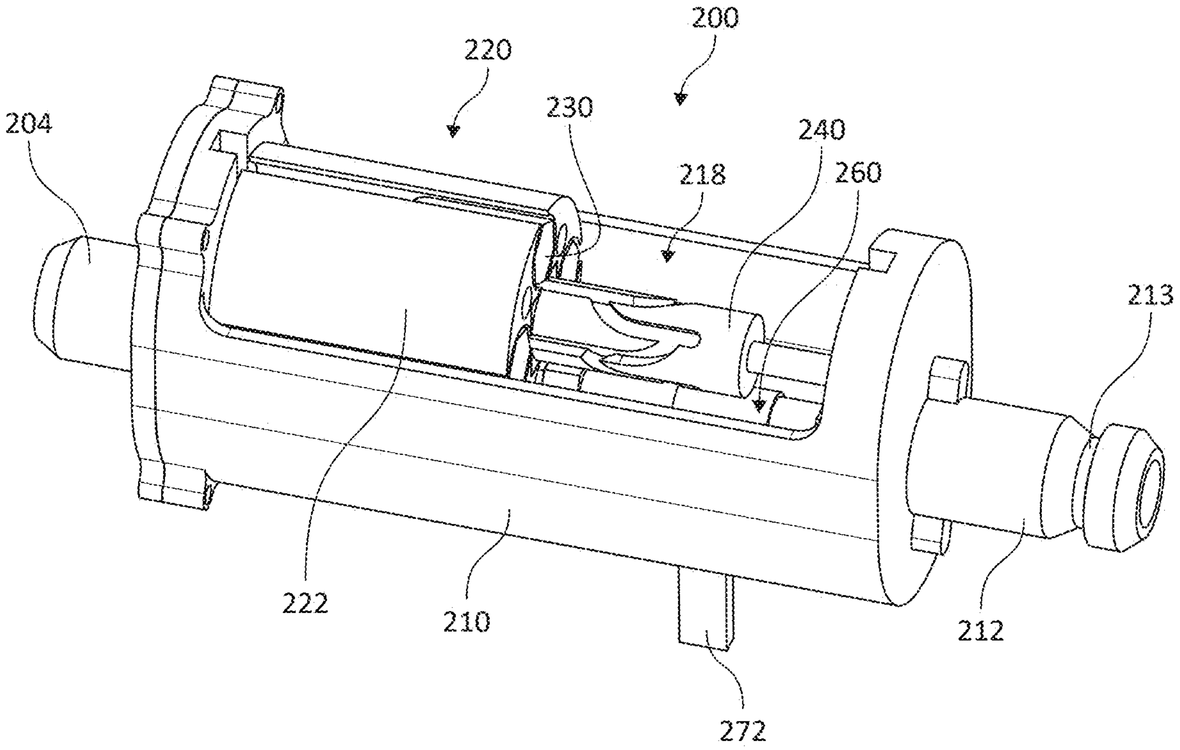
FIG. 10 is a perspective view of the cartridge and shaft module of FIG. 6 with a plurality of screw and drive-bit assemblies loaded in a screw cartridge.

Referring to FIG. 10, a perspective view of the cartridge and shaft module 200 is illustrated with screw and drive-bit assemblies 230 held in the screw cartridge 220. The handle 272 can be located more toward the proximal end of the cartridge and shaft module 200 as compared to the state shown in FIGS. 6-9. At the state shown in FIG. 10, no screw 232 is extending out of the delivery port 204, as shown in the state of FIG. 2. Again, the handle 272 can have a cap or knob for easy grasping.

Figure 11:
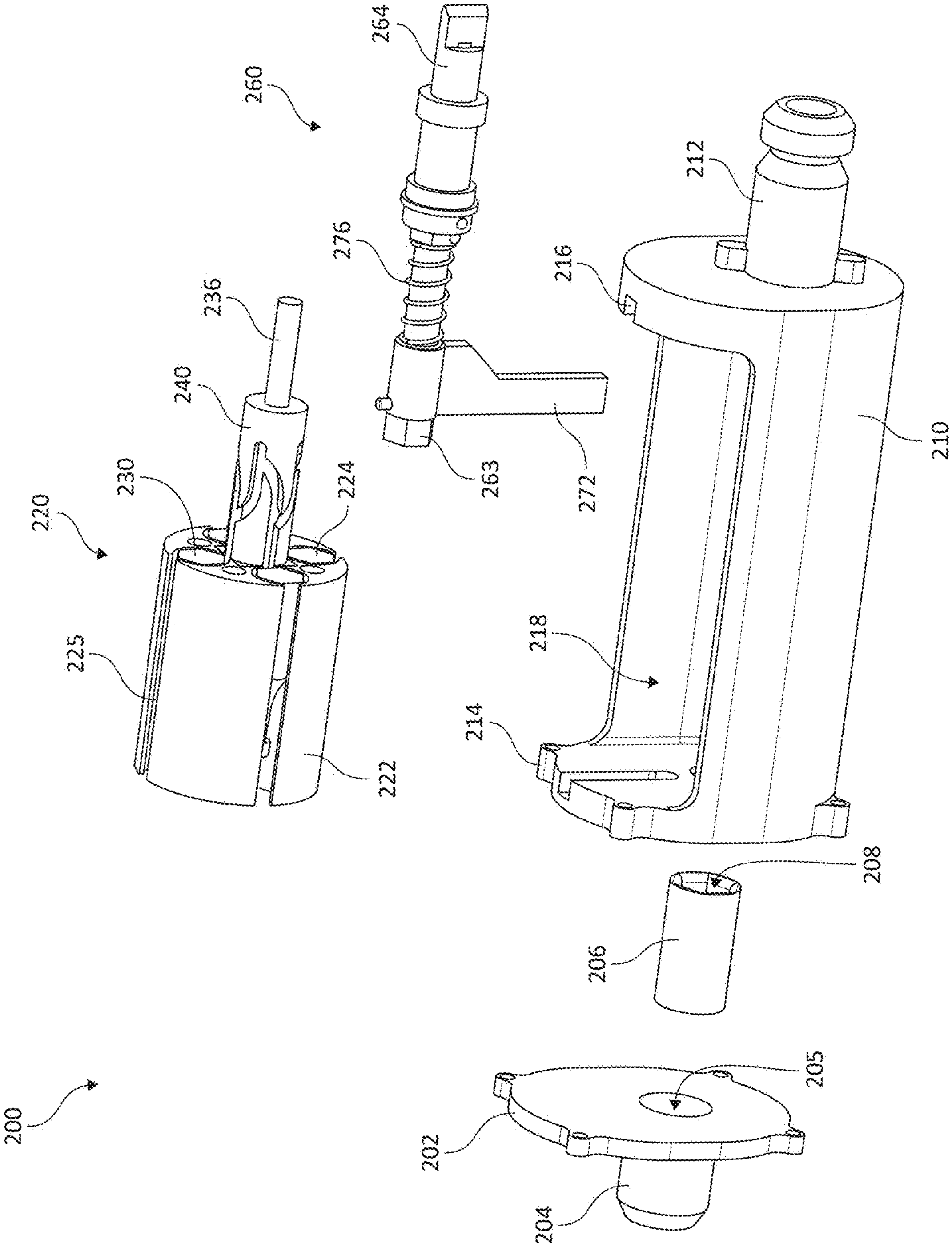
FIG. 11 is an exploded view of the cartridge and shaft module of FIG. 10, showing certain subassemblies and components.

FIG. 11 is an exploded view of the cartridge and shaft module 200 at the state of FIG. 10. It can be seen that the screw cartridge 220 comprises a cartridge barrel 222. The cartridge barrel 222 can be cylindrically shaped having a circular lateral surface bounded by a flat surface at the distal end and another flat surface at the proximal end. The cartridge barrel 222 can have a plurality (e.g., two, three, four, five, six, or more) barrel chambers 224 formed through the length in generally parallel with a centerline of the cartridge barrel 222. The centerline of the cartridge barrel 222 can be generally parallel to the longitudinal direction or axis 102. In some embodiments, the cartridge barrel 222 may contain more than four or another number of barrel chambers 224.

As shown in FIG. 11, each of the barrel chamber 224 can be configured to hold a screw and drive-bit assemblies 230 in the internal space. The screw and drive-bit assembly 230 can be consumed (e.g., used) during a screw delivery operation. An open slit 225 connects each barrel chamber 224 radially to outside.

In FIG. 11, the cartridge barrel 222 is integrated with a revolver cam 240 and a cartridge shaft 236 both of them substantially coaxial with the cartridge barrel 222. As such, when integrated the cartridge barrel 222, the cartridge barrel 222 and the revolver cam 240 can rotate with the cartridge shaft 236 around the axis of the cartridge shaft 236. The drive shaft assembly 260 comprises the distal shaft 262 with the handle 272 and a spring (e.g., a compression spring) 276 sleeved thereon and the proximal shaft 264.

A housing cap 202 is shown disposed at the distal end of the housing 210 with a port 204 protruding distally. In some embodiments, the port 204 comprises a loading port. The port 204 can have an internal port channel 205. The internal port channel 205 can be generally parallel to the longitudinal direction 102 and through the length of the port 204 and the housing cap 202. A shaft-to-drive-bit adaptor 206 is disposed in the internal port channel 205, as shown in FIG. 11 and in FIG. 9. When assembled, there exists a small gap between the shaft-to-drive-bit adaptor 206 and the internal port channel 205 of the port 204, so that the shaft-to-drive-bit adaptor 206 can rotate within the internal port channel 205 with minimal resistance. The shaft-to-drive-bit adaptor 206 can have an internal adapter channel 208 formed therein. As will be describe subsequently, the adaptor channel 208 has a shape to match the shape of head of the drive-bit 234 and the distal head 263 of the distal shaft 262. As such, when the distal shaft 262 advances distally pushing a screw and drive-bit 230 into the adaptor channel 208, the shaft-to-drive-bit adaptor 206 can facilitate or ensure that rotational movement and torque from the distal shaft 262 is effectively transferred to the drive-bit 262, and subsequently to the screw 232.

Figure 12:
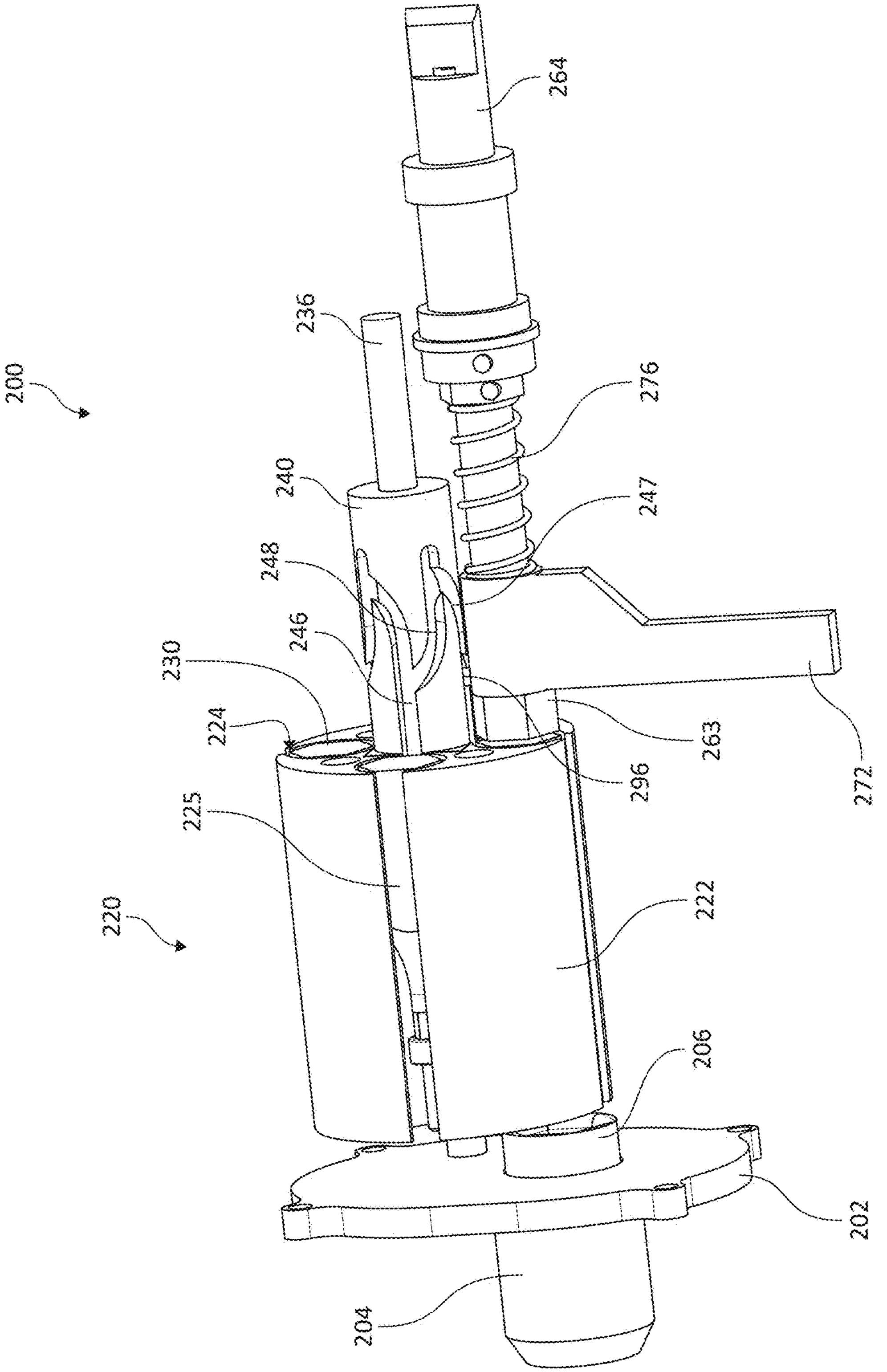
FIG. 12 is a perspective view of the of the cartridge and shaft module of FIG. 10 with the housing removed, wherein a handle is at a neutral position.
Figure 13:
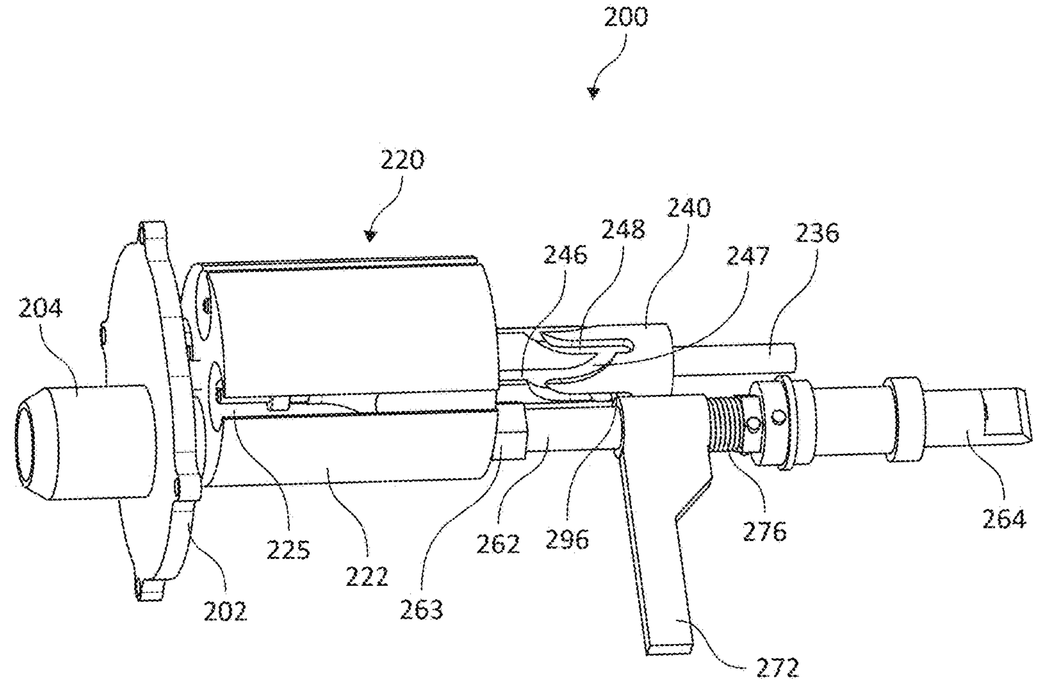
FIG. 13 is a perspective view of the of the cartridge and shaft module of FIG. 10 with the housing removed, wherein a handle is at a retracted position.
Figure 14:
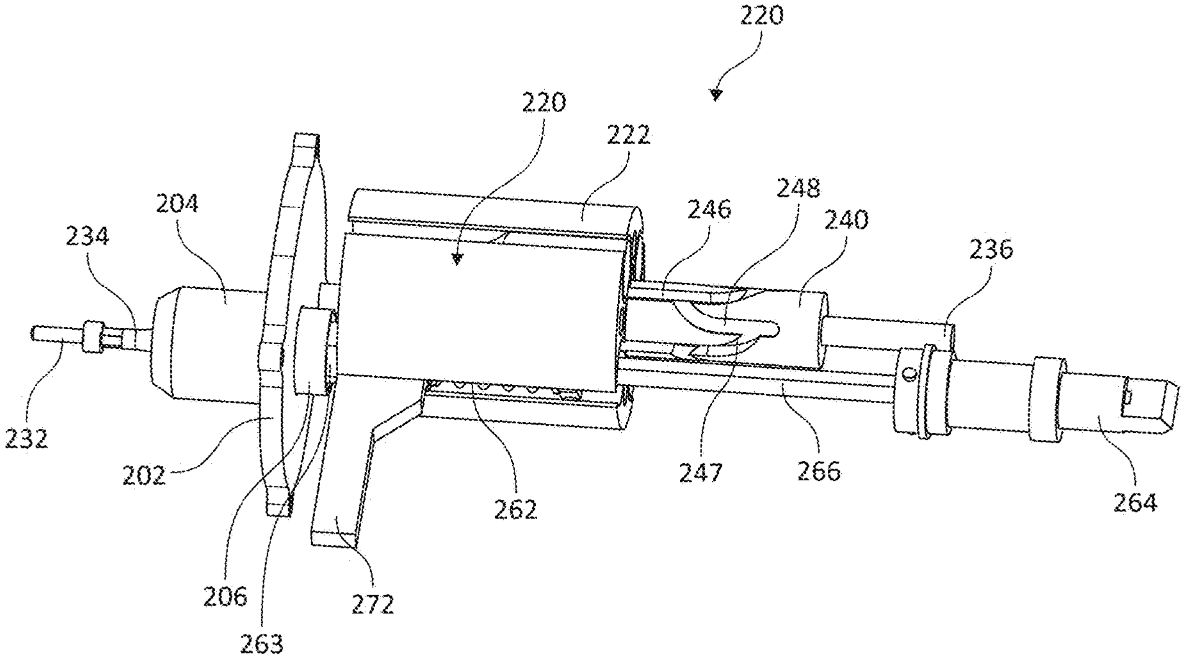
FIG. 14 is a perspective view of the of the cartridge and shaft module of FIG. 10 with the housing removed, wherein a handle and distal shaft are at a forward (also called extended) position.

Referring to FIGS. 12-14 to follow, the housing 210 is removed to reveal certain details of the cartridge and shaft module 200 when the handle 272 is at three different positions during the operation of the screw delivery system 100. In FIG. 12, the handle 272 is at a neutral position, corresponding to a state depicted in FIG. 2, FIG. 10, and FIG. 11, as explained previously. At the neutral position the compression spring 276 is naturally extended and the head 263 of the distal shaft 262 is adjacent or in touch with the proximal flat surface of the cartridge barrel 222. As can be seen, the distal shaft 262 is generally aligned with one of the barrel chambers 224 in the cartridge barrel 222. As such the head 263 of the distal shaft 262 is in touch with and/or substantially coaxially aligned with the head the drive-bit 234 held inside the barrel chambers 224. At this neutral position, the screw cartridge 220 is not restricted by the drive shaft assembly 260 and/or can be removed from the cavity 218 of the housing 210, e.g., for reloading screw and drive-bit assemblies 230. As shown in FIG. 12, a cam-pin 296 coupled with the handle 272 can be engaged into one of a plurality of straight groove portions 246 (e.g., four straight groove portions) on the cylindrical lateral surface of the revolver cam 240.

FIG. 13 shows a retracted position of the handle 272. In this position, the compression spring 276 can be compressed at a retracted length and/or the handle 272 can be located at a position toward the proximal shaft 264. This retracted position of the handle 272 is normally caused by moving the handle 272 sliding on the distal shaft 262 toward the proximal end, e.g., from pulling by the operation surgeon or an assistant, resulting the compression spring 276 to be compressed. As can be seen in FIG. 13, at the retracted position the cam-pin 296 can be engaged into and positioned at a proximal end of a second curved groove portion 248. During the process of pulling the handle 272, the cam-pin 296 travels proximally first along the straight groove portion 246, then enters into a first curved groove portion 247. The curvature of the first curved groove portion 247 causes the revolver cam 240 to rotate around the revolver shaft 236. Subsequently, the cam-pin 296 enters into the second curved groove portion 248, and eventually stops at the proximal end of the second curved groove portion 248.

When the handle 272 is released from the retracted position, the compression spring 276 extends to push the handle 272 to the neutral position shown in FIG. 12. However, the cam-pin travels distally along the second curved groove portion 248 and enters a straight groove portion 246. The curvature of the second curved groove portion 248 causes the revolver cam 240 to further rotate around the revolver shaft 236. When the handle 272 returns to the neutral position, the rotation of the revolver cam 240 causes the cartridge barrel 222 to stop at a rotational position so that the head 263 of the distal shaft 262 is substantially coaxially aligned with a barrel chamber 224 that is adjacent to the previous barrel chamber 224 before the handle 272 was moved to the retracted position. Therefore, the action of moving the handle 272 to the retracted position and then releasing it back to the neutral position allows the distal shaft 262 to be aligned with the next barrel chamber 224. In such a way, by repeating the action of moving the handle 272 to the retracted position and returning to the neutral position, the distal shaft 262 can be aligned (e.g., reciprocally, sequentially and/or serially) with every barrel chamber 224 inside the cartridge barrel 222.

FIG. 14 shows a forward position wherein the handle 272 is located at a position close to the housing cap 202 of the screw delivery system 100. This forward position was shown FIGS. 1, and 3-9. In FIG. 14, the handle 272 is positioned inside one of the plurality of (e.g., four) open slits 225 on the cylindrical lateral surface of a cartridge barrel 222. The open slits 225 can be linearly and/or generally parallel to the longitudinal direction 102, and/or can be connected to one of the barrel chambers 224 inside the cartridge barrel 222. The head 263 of the distal shaft 262 can be at least partially located inside the internal channel 208 of the shaft-to-drive-bit adaptor 206.

To transition from the neutral position shown in FIG. 12 to the forward position shown in FIG. 14, the handle 272 is pushed toward the distal end of the screw cartridge 200, entering into the linear open slit 225, as shown in FIG. 14. The forward movement of the handle 272 stops when the extension of the coupling shaft adaptor 266 exhausts, or when the handle 272 meets a hard stop. In some embodiments, the screw delivery system 100 may include a feature to secure the forward position so that the drive shaft assembly 260 is rigid lengthwise to insert the screw 232 into a patient.

3. Screw Cartridge

Figure 15:
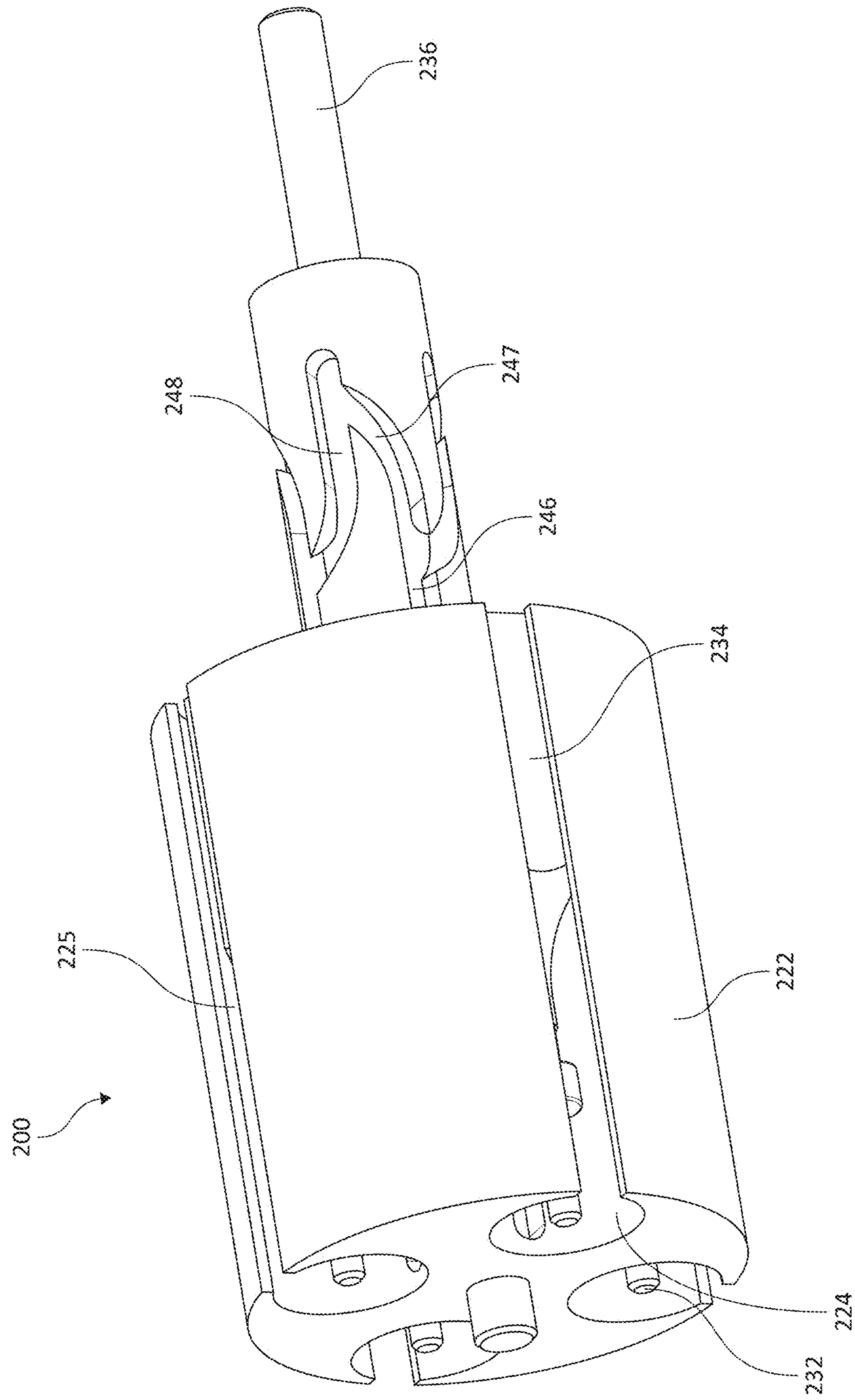
FIG. 15 is a perspective view of the screw cartridge disposed in the cartridge and shaft module of FIG. 10.
Figure 16:
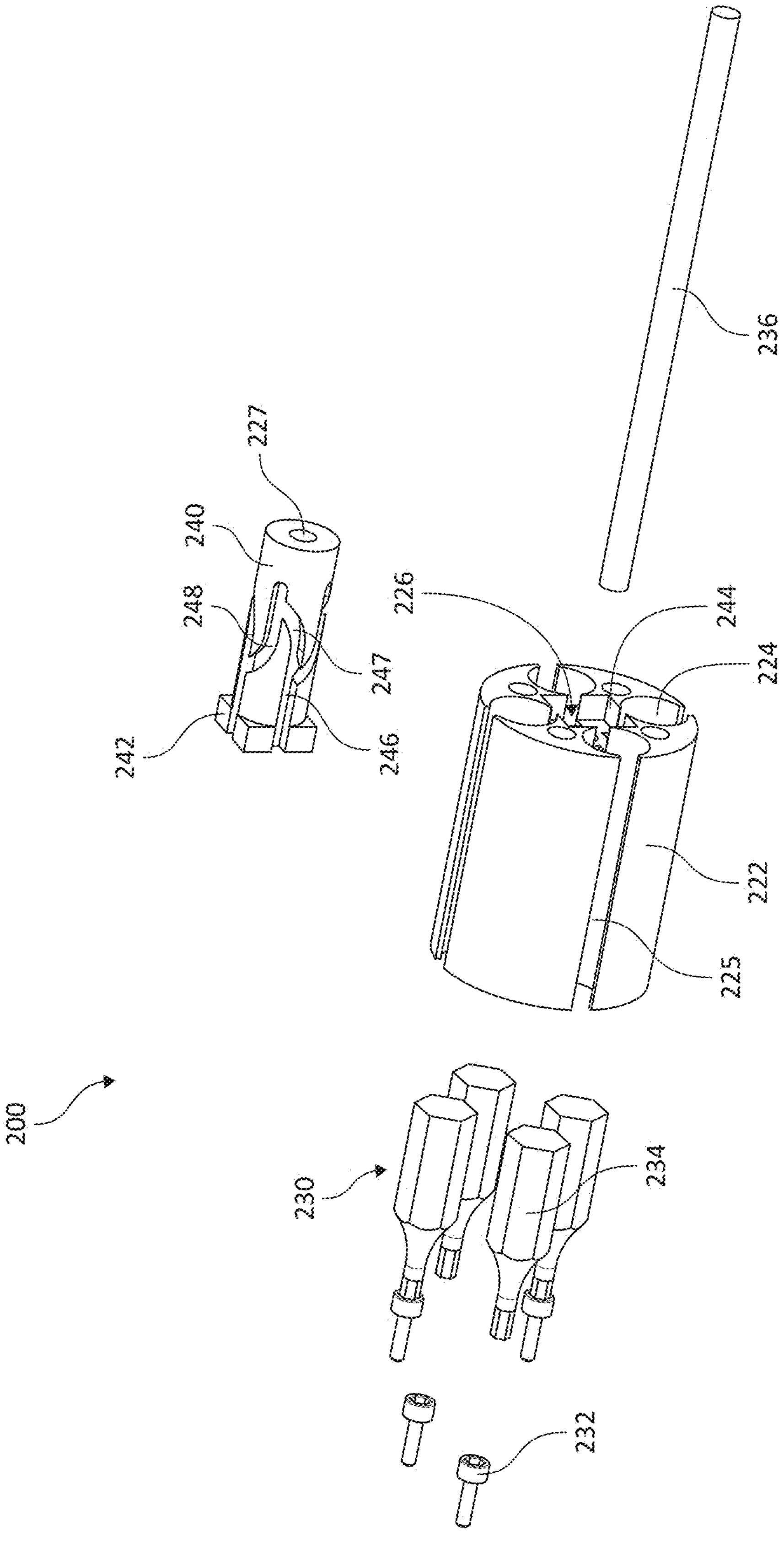
FIG. 16 is an exploded view of the screw cartridge of FIG. 15.

Referring to FIG. 15, the screw cartridge 220 is shown as a perspective view. An exploded view of the screw cartridge 220 is illustrated in FIG. 16, wherein the cartridge shaft 236 is configured to be coupled with a first cartridge shaft hole 226 along the centerline of the cartridge barrel 222, and a second cartridge shaft hole 227 along the centerline of the revolver cam 240. The revolver cam 240 comprises a polygonal (e.g., squared) head 242 that is configured to be coupled with a polygonal (e.g., squared) recess 244 on the proximal surface of the cartridge barrel 222. The head 242 and the squared recess 244 can take other shape, e.g., triangle or pentagon, as long as rotational movement can be effectively transferred from the revolver cam 240 to the cartridge barrel 222. The revolver cam 240 is shown to have straight groove portions 246, first curved groove portions 247, and second curved groove portions 248 thereon to engage the cam-pin 296 and to cause the cartridge barrel 222 to rotate when the handle 272 is moved from the neutral position to the retracted position and then back to the neutral position. However, the revolver cam 240 can be structured differently to perform the same functions.

As shown in FIG. 16, the barrel chambers 224 are cylindrical from the distal end to the proximal end of the cartridge barrel 222 with chamber centerlines generally parallel to the barrel centerline. The barrel chambers 224 can be uniformly distributed in the cartridge barrel 222 with equal distance from the centerline of the cartridge barrel 222 to centerline of each barrel chamber 224 and equal angular divisions between adjacent barrel chambers 224 with the barrel centerline as origin.

As shown in FIG. 15 and FIG. 16, a screw 232 and drive-bit 234 pair are assembled to form the screw and drive-bit assembly 230. The screw 232 and the drive-bit 234 may be held together by, for example, magnetic force and/or a friction fit between the tip of the screw bit 234 and a recess on the head of the screw 232. When loaded in a barrel chamber 224, the screw and drive-bit assembly 230 can be held by friction between the drive-bit 234 and the inner surface of the barrel chamber 224. The cartridge barrel 222 may be made of a rubber or elastomer material so that the barrel chamber 224 can be slightly smaller in size than the maximum diameter of the drive-bit 234 to cause a friction fit between the barrel chamber 224 and the drive-bit 234. The friction can be low enough that the screw and drive-bit assembly 230 can be loaded into the barrel chamber 224 manually or with a hand-held tool, and can be pushed distally out of the barrel chamber 224 and into the shaft-to-drive-bit adaptor 206 by the distal shaft 262 with a sufficiently small force, e.g., within 1 pound force (lbf), within ½ lbf, or with ¼ lbf. In some embodiments, the cartridge barrel 222 can be made of a rigid material, e.g., metal, ceramic, or hard plastic, and the inter surface of the barrel chambers 224 can comprise a soft material layer, e.g., soft rubber or foam, to achieve friction fit between the barrel chamber 224 and the drive-bit 234.

In some embodiments, the cartridge barrel 222 can take other shapes. For example, the cartridge barrel 222can be rectangular shaped, such as with barrel chambers 224 uniformly distributed along one of the rectangular sides and/or with equal distances between adjacent barrel chambers 224. In some variants, the cartridge barrel 222 is pentagonal, hexagonal, octagonal, or shaped otherwise.

4. Drive Shaft

Figure 17:
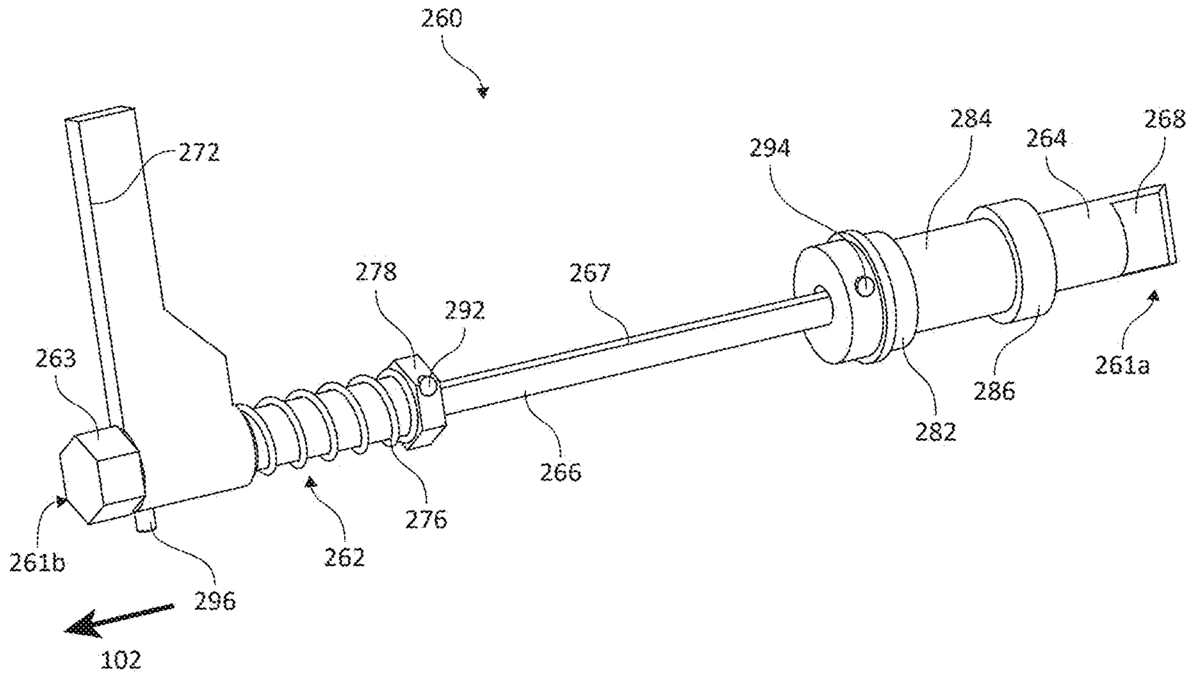
FIG. 17 is a perspective view of the driving shaft assembly disposed in the cartridge and shaft module of FIG. 10.
Figure 18:
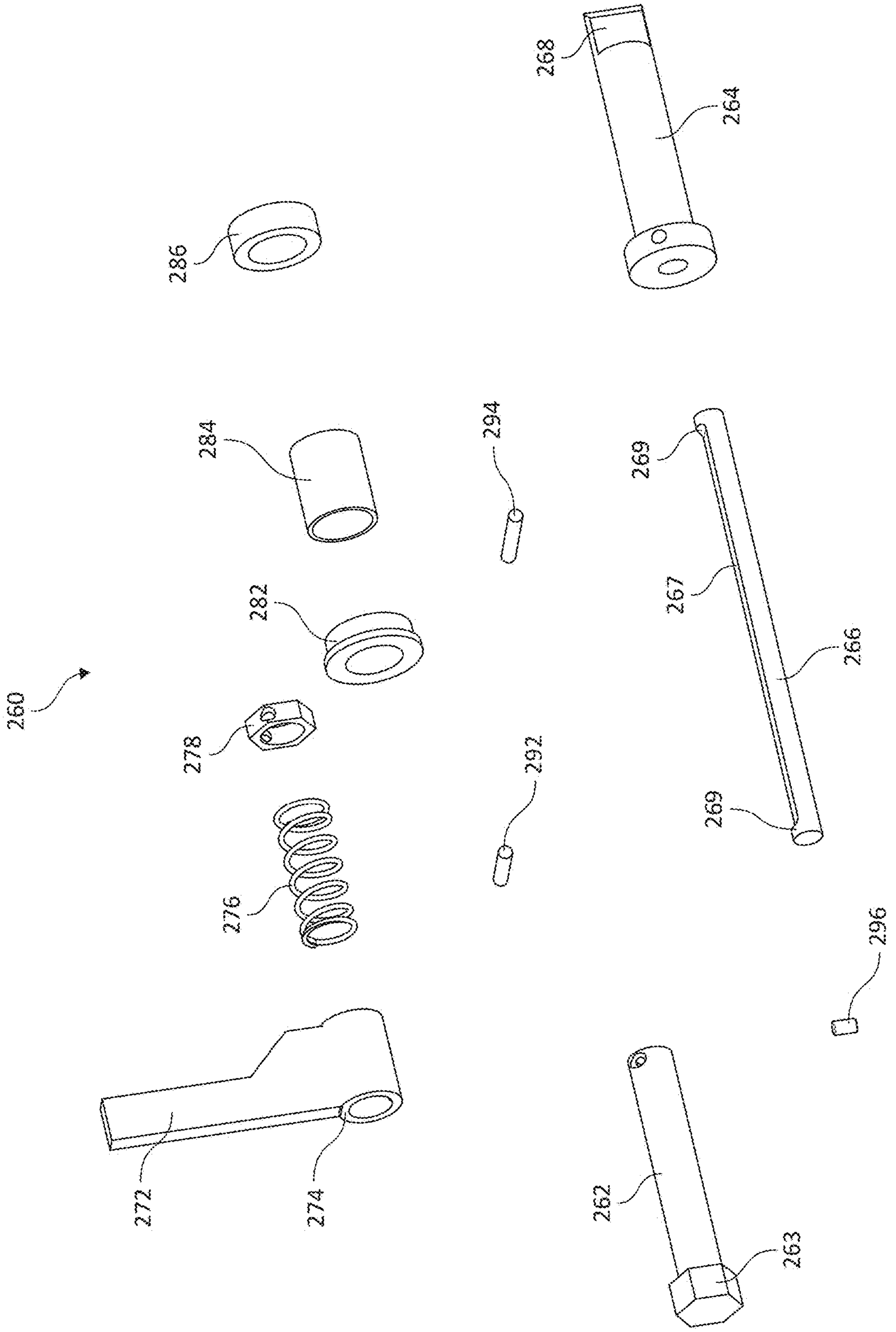
FIG. 18 is an exploded view of the driving shaft assembly of FIG. 17.

Moving to FIG. 17, the drive shaft assembly 260 is illustrated with the distal shaft 262 and the proximal shaft 264 extendably coupled by the shaft adaptor 266. The drive shaft assembly 260 has a proximal shaft end 261*a* and a distal shaft end 261*b*. The direction from the proximal shaft end 261*a* to the distal shaft end 261*b* is parallel to the longitudinal direction 102. FIG. 18 is an exploded view of the drive shaft assembly 260, showing components involved. Viewing FIG. 17 together with FIG. 18, multiple (e.g., three) parts are sleeved on the distal shaft 262, such as including the handle 272 which can be connected to a tubular portion 274, the compression spring 276, and a shaft collar 278 which can be attached to the proximal end of the distal shaft 262 by a first shaft pin 292. As described before, when assembled the handle 272 can slide on the distal shaft 262. The handle 272 is naturally biased by the compression spring 276 distally to press on the head 263 of the distal shaft 262. The distal shaft 262 can rotate within the handle 272 and the compression spring 276 with minimal frictional resistance.

On the proximal shaft 264 can be sleeved multiple (e.g., three) parts, a flange bearing 282, a spacer 284, and a second bearing 286. The flange gear 282 is restricted by the distal head on the proximal shaft 264. When assembled in the housing 210, the flange gear 282 and the second bearing 286 can facilitate or ensure that the proximal shaft 264 is firmly held in the housing 210 and can freely rotate. The proximal shaft 264 has a proximal head 268 configured to be coupled to the motor shaft 136 with the shaft coupler 138 when the cartridge and shaft module 200 can be attached to the screwdriver body 130. As illustrated, the proximal head 268 can have a flat screwdriver shape. The proximal head 268 can take other shapes, as long as rotational movement and torque can be transferred from the motor 134 to the drive shaft assembly 260 through the shaft coupler 138.

In an intermediate section, such as the middle, of the drive shaft assembly 260 is the shaft adaptor 266. The shaft adaptor 266 has a partial recess or cut out forming a generally flat surface 267. At each end of the shaft adaptor 266 there can be a sloped edge 269 expanding the shaft from a partial cylinder of the central portion to a full or near full cylinder at each end portion. Each of the distal shaft 262 and the proximal shaft 264 has a hole along its centerline to accept the shaft adaptor. When assembled with the distal shaft 262, the distal end of the shaft adaptor 266 is constrained by the first pin 292 that is inserted in a hole in the shaft collar 278 and the proximal end of the distal shaft 262, because the first pin 292 is in touch with the flat surface 267 of the shaft adaptor 266. As such, the distal head of the shaft adaptor 266 is stopped by the first pin 292 at the sloped surface 269 and cannot come out of the central hole in the distal shaft 262. The proximal end of the shaft adaptor 266 is constrained by the second pin 294 that is inserted into a hole on the distal end head of the proximal shaft 264 in the same way that the distal head of the shaft adaptor 266 is retrained by the first pin 292. As such the drive shaft assembly 260 is extendable lengthwise. In some embodiments, the engagement of the first pin 292 and the second pin 294 with the flat surface 267can facilitate that the drive shaft assembly is rotationally rigid, able to transfer rotational movement and torque to the drive-bit 234 and the screw 232.

5. Operation

Back to FIG. 2, when loaded with the screw cartridge 220, the screw delivery system 100 is ready to be used, such as in a surgical or other medical operation. The user, e.g., a surgeon, can move the handle 272 distally to the forward or extended position. The movement can cause the distal shaft 262 to advance, thereby pushing a screw and drive-bit assembly 230 into the shaft-to-drive-bit adaptor 206 which is disposed in the port 204, as illustrated in FIG. 1 and FIGS. 6-10. The screw and drive bit assembly 230 can be exposed. The user (e.g., surgeon) can observe if a screw 232 is pushed out of the delivery port 204. This position (with the screw pushed out of the port) can be a ready-to-install position of the screw. In various embodiments, in the ready-to-install position, some or all of the screw 232 is exposed and/or is visible to the user, such as the distal tip; the distal tip and the threads; the distal tip, threads, and proximal head; etc. This can allow the user to confirm the screw details (e.g., size, quality, material, type etc.) before inserting the screw and/or in increase accurately in placing the screw in the patient (e.g., compared to a system in which the screw is hidden from view). The user can proceed to insert the screw into the patient as part of the surgical operation. In some embodiments, the surgeon may enable a securing feature to hold the drive shaft assembly 260 at the forward position during screw insertion.

If no screw is observed outside of the delivery port 204, it means that the barrel chamber 224 the distal shaft 262 advanced into is empty. Then the user pulls the handle 272 proximally to the retracted position and releases the handle 272 so that the handle 272 moves distally to the neutral position. As described above, the action of moving the handle 272 proximally to the retracted and releasing it to the neutral position causes the revolver cam 240 to rotate and bring the next barrel chamber 224 aligned with the distal shaft 262. As such, the cartridge barrel 222 is indexed rotationally by one barrel chamber 224 position. For example, in the illustrated embodiment with four chambers, each pull and release of the handle 272 rotates the cartridge barrel 222 about 90°. In some embodiments, each pull and release rotates the cartridge barrel 222 at least about: 30°, 45°, 60°, 120°, or otherwise.

The user can repeat the process steps of pushing the handle 272 distally to the forward position and observing if a screw 232 comes out of the delivery port 204, as described above. If the answer is yes, he can proceed to insert the screw into the patient. The user may sequentially repeat the steps until all of the screw and drive-bit assemblies 230 held in the screw cartridge 220 are consumed. If no screw is observed outside the delivery port 204, it means that the screw cartridge 220 is empty (containing no more screw and drive-bit assemblies 230). The empty cartridge 220 can be replaced and reloaded with a non-empty screw cartridge 220. In some embodiments, this occurs by a user (e.g., a surgical assistant) pulling the current screw cartridge 220 out of the housing 210 and installing a new screw cartridge 220 into the housing 210. The user can check that both ends of the cartridge shaft 236 are snapped or otherwise secured in the snap or securing features in the first and second channels 214, 216. The screw delivery system 100 can be used to continue the operation or procedure.

6. Alternative Embodiment

Figure 19:
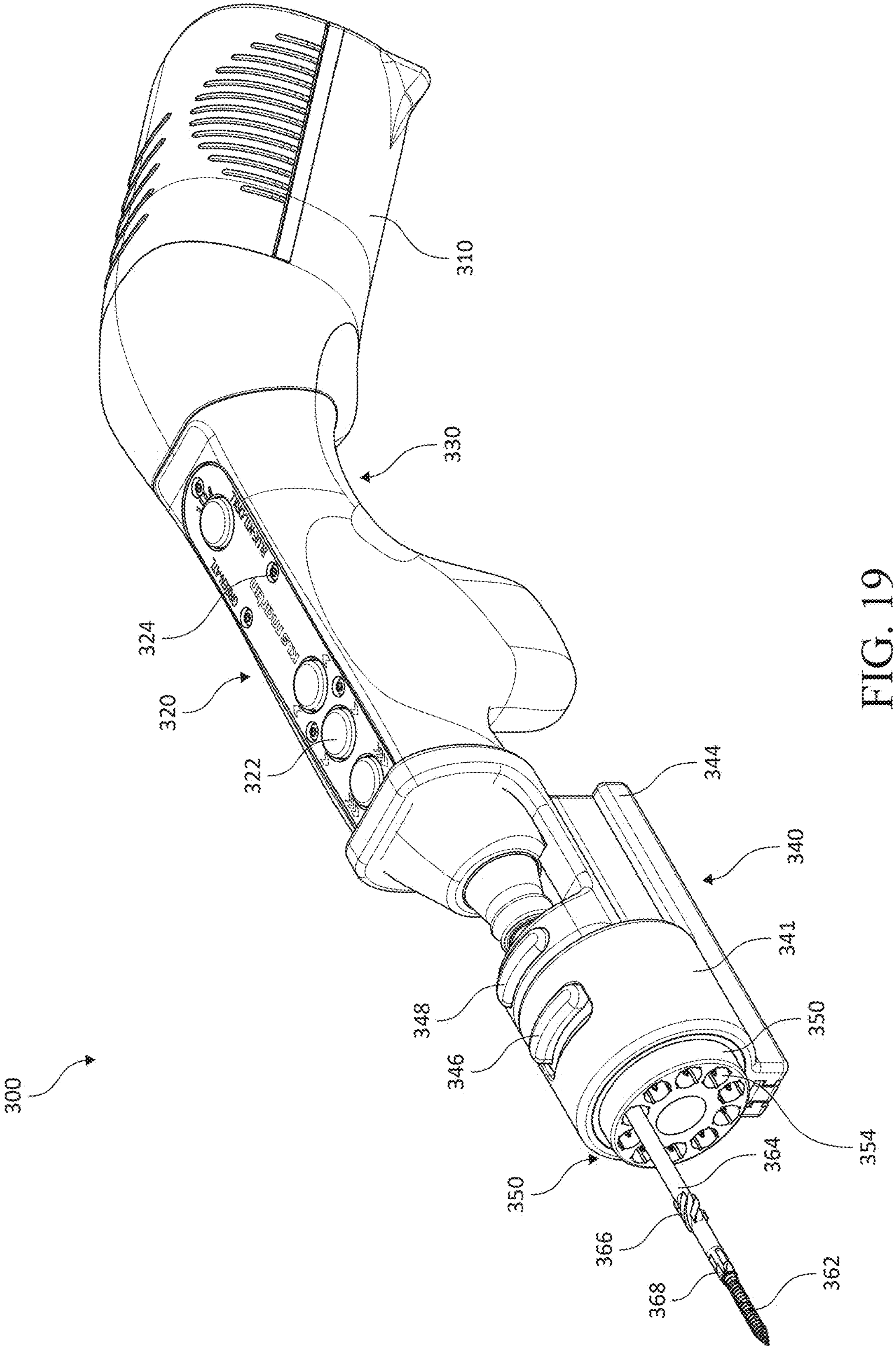
FIG. 19 is a perspective view of an embodiment of another screw delivery system with a screw loaded from a screw cartridge to a drive shaft ready for operation.

FIG. 19 shows a perspective view of a screw delivery system 300 that is an alternative embodiment of the screw delivery system 100 shown in FIG. 1. Similar to the screw delivery system 100 of FIG. 1, the screw delivery system 300 comprises a handgrip 310, a control panel 320 having a plurality of buttons 322 and a plurality of LED signals 324, and a screw driver body 330. The screw delivery system 300 can comprise a cartridge and shaft module 340 that is detachable from the screw driver body 330. The screw cartridge 350 in FIG. 19 has ten barrel chambers 354, but can be constructed to have more or less barrel chambers.

Figure 20:
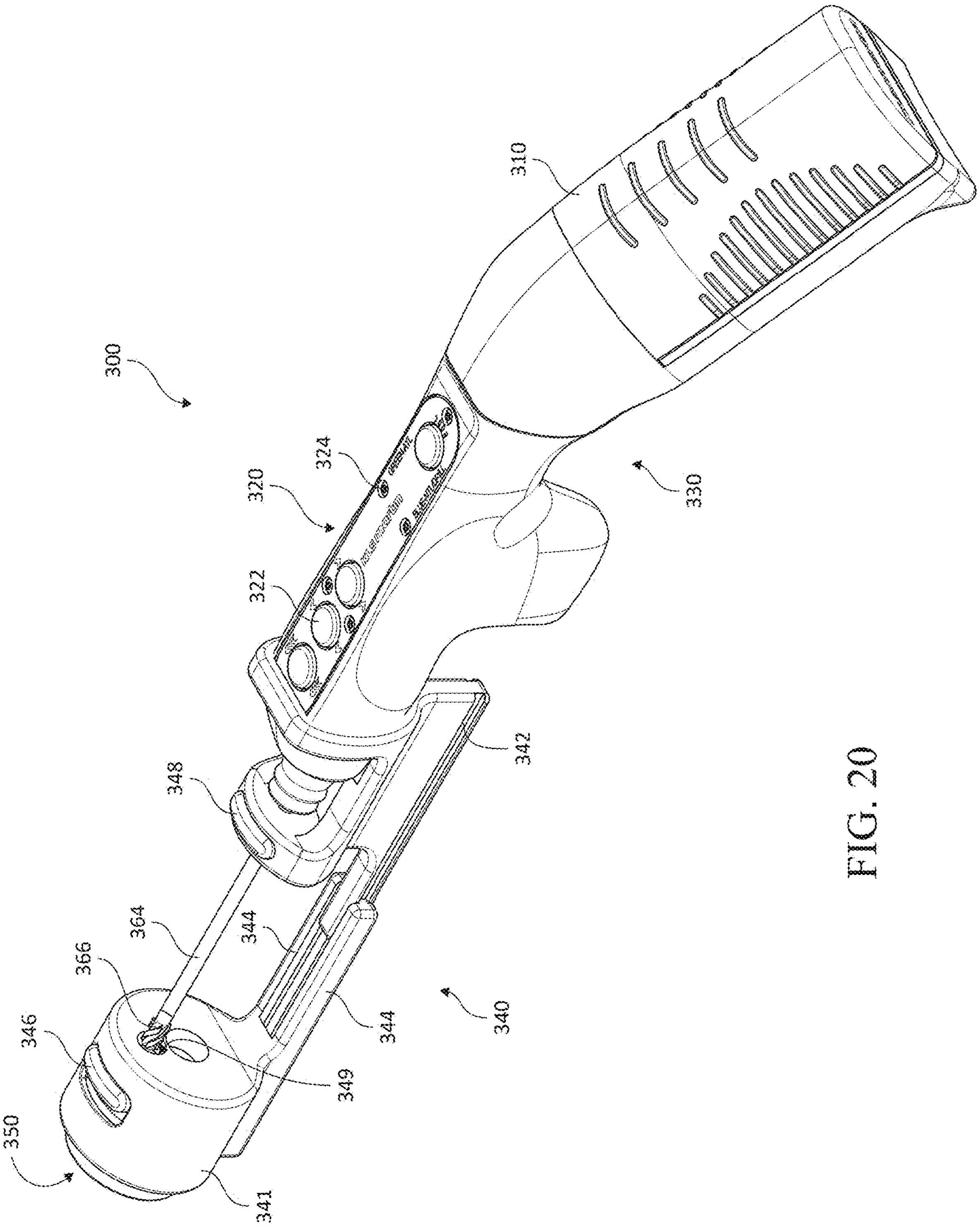
FIG. 20 is a perspective view of the screw delivery system of FIG. 19 with the screw shaft at a neutral position.

FIG. 20 is another perspective view of the screw delivery system 300 shown in FIG. 19. However, the cartridge and shaft module 340 shown in FIG. 19 and FIG. 20 are in different positions. In FIG. 19, the cartridge housing 341 is retracted, allowing a screwdriver shaft 364 to penetrate through and extend out of one of the barrel chambers 354 in a screw cartridge 350.

The cartridge and shaft module 340 in FIG. 20 is at an extended position. As can be seen, a tip 368 of the screwdriver shaft 364 can be coupled with a screw 362, ready to insert the screw 362 into a patient. The cartridge housing 341 can be slidable distally and proximally when sliders 344 are engaged and sliding in the rail channels 342 on both sides of the screw delivery system 300. At the extended position shown in FIG. 20, the tip 368 of the screwdriver shaft 364 is disposed in a channel 345 of the cartridge housing 341, but majority portion of the screwdriver shaft 364 can be located outside of the cartridge housing 341.

The distal end of the shaft can have helically shaped guiding features 366. The guiding features 366 can help to engage the tip 368 of the screwdriver shaft 364 with the screw 362 for smooth coupling.

Also shown in FIG. 19 and FIG. 20 are a first button 346 and a second button 348 coupled with the cartridge and shaft module 340. The first button 346 may have the function to index-step rotate the screw cartridge 350 so that the screwdriver shaft 364 can access all barrel chambers 354. In some embodiments, moving the first button 346 distally and proximally may index-step rotate the screw 350. In some embodiments, the first button 346 may function to engage or release the screw cartridge 350, e.g., by pushing the first button 346 down. The second button 348 may have the function to engage or lease the screwdriver shaft 364.

Figure 21:
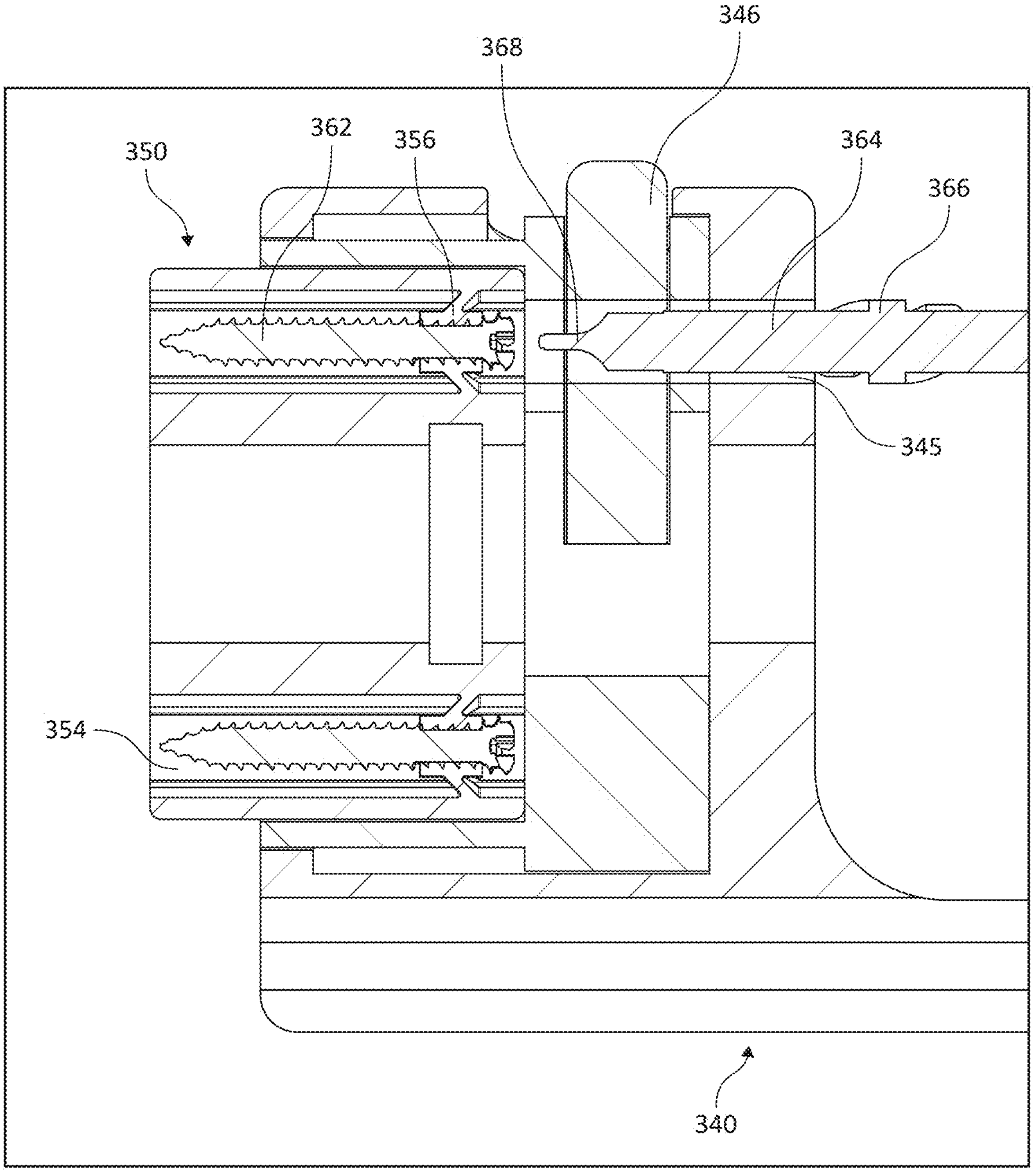

FIG. 21 is a partial cross-sectional view showing certain internal structures of the cartridge and shaft module 340 at the extended position shown in FIG. 20, including the screw cartridge 350 and the screwdriver shaft 364. As can be seen, the screw cartridge 350 is coupled with the cartridge and shaft housing 340 at the distal end. In this arrangement, the barrel chambers 354 in the screw cartridge 350 are exposed at the distal end. An internal channel 345 can be substantially centered with a screw 362 held in a barrel chamber 354 located close to the top of the screw cartridge 350. When the tip 368 of the screwdriver shaft 364 enters into the internal channel 345, the guiding features 366 can facilitate or ensure that the tip 368 is substantially centered with the internal channel 345 and engaged with the screw 362.

The internal channel 345 may have helical grooves on the internal surface. When the tip 368 enters the internal channel 345 and moves axially toward the screw 362, the engagement of the helical guide features 366 with the helical grooves in the internal channel 345 may cause the tip 368 to slowly rotate. This can be a first stage of engagement. When the tip 368 contacts the screw 362 and begins pushing the screw 362, the slow rotation of the tip 368 relative to the screw 362 helps the tip 368 to locate and mate with head of the screw 362. This can be a second stage of engagement. Subsequently, the tip 368 and screw 362 are pushed out of the internal channel 345, thereby exposing the screw and/or the bit. This can be a third stage of engagement. When the engagement between the helical features 366 and the helical grooves in the internal channel 345 stops, the slow rotation of the tip 368 stops. In some embodiments, such stopping of the slow rotation can occur in the second stage of engagement; in some embodiments, such stopping of the slow rotation can occur in the third stage of engagement. The powered screwdriver 300 can be actuated by the user to insert the exposed screw into the patient.

In some embodiments, in a first stage, the tip enters the channel and moves axially toward the screw and rotates relative to the screw. The rotation can be caused by the helical guide features engaging with corresponding helical features in the channel. In some embodiments, in a second stage, the tip contacts the screw and begins pushing the screw, but also continues to rotate relative to the screw (which can aid in locating the bit in the screw head). In some embodiments, in a third stage, the tip and screw push out of the channel and stop rotating until the powered screwdriver is actuated to insert the screw into the patient.

In some embodiments, inside each barrel chamber 354 there can be a grasping feature 356 configured to hold the screw 362 when engaged. The grasping feature 356 can be made of a resilient material, e.g., rubber, or is a spring made of metal or plastic. As such, when the tip 268 of the screwdriver shaft 364 is coupled with the screw 362, it can push the screw 362 distally out of the barrel chamber 354 as the resilient grasping feature 356 flexes outward. The screw 362 and the tip 268 of the screwdriver shaft 364 stay together may be by magnetic force and/or friction fit between the bit and a recess on the head of the screw 362.

7. Certain Terminology

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees and the term "generally perpendicular" can refer to something that departs from exactly perpendicular by less than or equal to 20 degrees.

Unless otherwise explicitly stated, articles such as "a" or "an" should generally be interpreted to include one or more described items. Accordingly, phrases such as "a device configured to" are intended to include one or more recited devices. Such one or more recited devices can be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

8. Summary

The technology of the present disclosure has been discussed in the context of certain embodiments and examples. The technology extends beyond the specifically disclosed embodiments to other alternative embodiments and/or uses of the embodiments and certain modifications and equivalents thereof. For example, although certain embodiments are disclosed in the context of a screw delivery system or powered screwdriver, the technology can be applied to other fastener delivery tool too. Any two or more of the components of the screw delivery system can be made from a single monolithic piece or from separate pieces connected together. Various features and aspects of the disclosed embodiments can be combined with or substituted for one another in order to form varying modes of the invention. The scope of this disclosure should not be limited by the particular disclosed embodiments described herein.

Certain features that are described in this disclosure in the context of separate implementations can also be implemented in combination in a single implementation. Conversely, various features that are described in the context of a single implementation can also be implemented in multiple implementations separately or in any suitable subcombination. Although features may be described above as acting in certain combinations, one or more features from a claimed combination can, in some cases, be excised from the combination, and the combination may be claimed as any subcombination or variation of any subcombination.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying drawings. The figures are drawn to scale, but such scale is not limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

In summary, various embodiments and examples of screw delivery systems and related methods have been disclosed. Although the screw delivery systems have been disclosed in the context of those embodiments and examples, the technology of this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described above, but should be determined only by a fair reading of the claims that follow.

The following is claimed:

1. A surgical screw delivery apparatus comprising:

a housing configured to be attached to a powered surgical screwdriver;

a shaft assembly coupled with the housing, the shaft assembly having a proximal end, a distal end, and a longitudinal axis;

a screw cartridge coupled with the housing, the screw cartridge comprising a cartridge barrel, the cartridge barrel having a plurality of barrel chambers each configured to hold a screw; and a handle configured to slide in a direction generally parallel to the longitudinal axis between a first position and a second position;

wherein the distal end of the shaft assembly is coaxially aligned with one of the plurality of barrel chambers, and wherein each time the handle is moved from the first position to the second position the screw cartridge is rotationally indexed from one of the barrel chambers to another of the barrel chambers being aligned with the shaft assembly.

2. The apparatus of claim 1, wherein the housing has a cavity, and wherein the screw cartridge and the shaft assembly are disposed in the cavity.

3. The apparatus of claim 2, wherein the cartridge barrel is cylindrically shaped with a barrel centerline generally parallel to the longitudinal axis, and wherein the plurality of barrel chambers are formed through the cartridge barrel with centerline of each barrel chamber generally parallel to the barrel centerline, and are uniformly angularly distributed within the cartridge barrel.

4. The apparatus of claim 3, wherein the screw cartridge further comprises a cylindrically shaped revolver cam coaxial with the cartridge barrel, the revolver cam having curved grooves formed thereon.

5. The apparatus of claim 4, wherein the screw cartridge further comprises a cartridge shaft coaxial with the cartridge barrel, each end of the cartridge shaft removably coupled with a securing feature disposed about the housing.

6. The apparatus of claim 5, wherein the shaft assembly comprises a distal shaft at the distal end and a proximal shaft at the proximal end, the distal shaft having a handle sleeved thereon allowing the distal shaft to rotate therein, wherein a cam-pin is coupled to the handle and engaged with curved grooves on the revolver cam, and wherein moving the handle proximally to a retracted position and then distally to a neutral position causes the cartridge barrel to rotate around the barrel centerline to a position so that the shaft assembly is indexed and coaxially aligned with the next barrel chamber within the cartridge barrel.

7. The apparatus of claim 6, wherein a compression spring is sleeved on the distal shaft adjacent and proximal to the handle biasing the handle toward the distal end of the distal shaft.

8. The apparatus of claim 6, wherein a port is disposed about the distal end of the housing, the port being substantially coaxial with the shaft assembly and configured to allow the screw to pass therethrough.

9. The apparatus of claim 8, wherein the distal shaft and the proximal shaft are extendably coupled by a shaft coupler so that the shaft assembly is extendable lengthwise but rigid rotation wise, and wherein moving the handle distally to a forward position pushes the distal end of the distal shaft at least partially in the port.

10. The apparatus of claim 9, wherein the screw is pre-assembled with a drive-bit, wherein a shaft-to-drive-bit coupler is disposed in the port, both an inner surface of the port and an outer surface of the shaft-to-drive-bit coupler are cylindrical shaped, allowing the shaft-to-drive-bit coupler to rotate within the port, and wherein the shaft-to-drive-bit coupler has a prism shaped internal channel matching an external prism shape of the distal end of the distal shaft and an external prism shape of the drive-bit.

11. The apparatus of claim 6, wherein the proximal shaft is coupled with a bearing, and wherein the bearing is coupled to the housing allowing the proximal shaft freely rotating therein.

12. The apparatus of claim 11, wherein the proximal end of the proximal shaft is flat shaped.

13. A power screwdriver, comprising:

a handgrip;

a screwdriver body, the screwdriver body having a proximal end, a distal end, and a longitudinal axis;

a control panel comprising a user input and a light signal; and a detachable cartridge and shaft module, the detachable cartridge and shaft module comprising:

a housing configured to be attached to the screwdriver body;

a shaft assembly coupled with the housing; and a screw cartridge coupled with the housing, the screw cartridge comprising a cartridge barrel, the cartridge barrel having a plurality of barrel chambers each configured to hold a screw;

wherein the distal end of the shaft assembly is coaxially aligned with one of the plurality of barrel chambers;

wherein the housing has a cavity, the screw cartridge and the shaft assembly disposed in the cavity of the housing;

wherein the cartridge barrel is cylindrically shaped with a barrel centerline generally parallel to the longitudinal axis, and wherein the plurality of barrel chambers are formed through the cartridge barrel with centerline of each barrel chamber generally parallel to the barrel centerline, and are uniformly angularly distributed within the cartridge barrel;

wherein the screw cartridge further comprises a cylindrically shaped revolver cam coaxial with the cartridge barrel and a cartridge shaft coaxial with the cartridge barrel, the revolver cam having curved grooves formed thereon, each end of the cartridge shaft removably coupled with a snap feature disposed about the housing; and wherein the shaft assembly comprises a distal shaft at the distal end and a proximal shaft at the proximal end, the distal shaft having a handle sleeved thereon allowing the distal shaft to rotate therein, wherein a cam-pin is coupled to the handle and engaged with curved grooves on the revolver cam, and wherein moving the handle proximally to a retracted position and then distally to a neutral position causes the cartridge barrel to rotate around the barrel centerline to a position so that the shaft assembly is indexed and coaxially aligned with the next barrel chamber within the cartridge barrel.

14. The power screwdriver of claim 13, wherein a port is disposed about the distal end of the housing, the port being substantially coaxial with the shaft assembly and configured to allow the screw to pass therethrough, wherein the distal shaft and the proximal shaft are extendably coupled by a shaft coupler so that the shaft assembly is extendable lengthwise but rigid rotation wise, and wherein moving the handle distally to a forward position pushes the distal end of the distal shaft at least partially in the port.

15. The power screwdriver of claim 14, wherein the screw configured to be held in the barrel chambers is pre-assembled with a drive-bit, wherein a shaft-to-drive-bit coupler is disposed in the port, both an internal surface of the port and an outer surface of the shaft-to-drive-bit coupler are cylindrical shaped, allowing the shaft-to-drive-bit coupler to rotate within the port, and wherein the shaft-to-drive-bit coupler has a prism shaped internal channel matching an external prism shape of the distal end of the distal shaft and an external prism shape of the drive-bit.

16. A surgical screw delivery apparatus comprising:

a housing configured to be attached to a powered surgical screwdriver;

a shaft assembly coupled with the housing, the shaft assembly having a proximal end, a distal end, and a longitudinal axis; and a screw cartridge coupled with the housing, the screw cartridge comprising a cartridge barrel, the cartridge barrel having a plurality of barrel chambers each configured to hold a screw;

wherein the distal end of the shaft assembly is coaxially aligned with one of the plurality of barrel chambers;

wherein the housing has a cavity, and wherein the screw cartridge and the shaft assembly are disposed in the cavity;

wherein the cartridge barrel is cylindrically shaped with a barrel centerline generally parallel to the longitudinal axis, and wherein the plurality of barrel chambers are formed through the cartridge barrel with centerline of each barrel chamber generally parallel to the barrel centerline, and are uniformly angularly distributed within the cartridge barrel;

wherein the screw cartridge further comprises a cylindrically shaped revolver cam coaxial with the cartridge barrel, the revolver cam having curved grooves formed thereon;

wherein the screw cartridge further comprises a cartridge shaft coaxial with the cartridge barrel, each end of the cartridge shaft removably coupled with a securing feature disposed about the housing; and wherein the shaft assembly comprises a distal shaft at the distal end and a proximal shaft at the proximal end, the distal shaft having a handle sleeved thereon allowing the distal shaft to rotate therein, wherein a cam-pin is coupled to the handle and engaged with curved grooves on the revolver cam, and wherein moving the handle proximally to a retracted position and then distally to a neutral position causes the cartridge barrel to rotate around the barrel centerline to a position so that the shaft assembly is indexed and coaxially aligned with the next barrel chamber within the cartridge barrel.

17. A power screwdriver, comprising:

a handgrip;

a screwdriver body, the screwdriver body having a proximal end, a distal end, and a longitudinal axis;

a control panel comprising a user input and a light signal; and a detachable cartridge and shaft module, the detachable cartridge and shaft module comprising:

a housing configured to be attached to the screwdriver body;

a shaft assembly coupled with the housing;

a screw cartridge coupled with the housing, the screw cartridge comprising a cartridge barrel, the cartridge barrel having a plurality of barrel chambers each configured to hold a screw; and a handle configured to slide in a direction generally parallel to the longitudinal axis between a first position and a second position;

wherein the distal end of the shaft assembly is coaxially aligned with one of the plurality of barrel chambers, and wherein each time the handle is moved from the first position to the second position the screw cartridge is rotationally indexed from one of the barrel chambers to another of the barrel chambers being aligned with the shaft assembly.

* * * * *